US006943162B2

(12) United States Patent
Hale et al.

(10) Patent No.: US 6,943,162 B2
(45) Date of Patent: Sep. 13, 2005

(54) PIPERAZINYLTRIAZINES AS ESTROGEN RECEPTOR MODULATORS

(75) Inventors: Ronnie Lee Hale, Woodside, CA (US); Brad Richard Henke, Durham, NC (US); Millard Hurst Lambert, III, Durham, NC (US); Amy Tsai Lu, Los Altos, CA (US); Paul Kenneth Spearing, Durham, NC (US); Philip Stewart Turnbull, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 59 days.

(21) Appl. No.: 10/466,847

(22) PCT Filed: Jan. 23, 2002

(86) PCT No.: PCT/US02/01758

§ 371 (c)(1),
(2), (4) Date: Jul. 21, 2003

(87) PCT Pub. No.: WO02/072561

PCT Pub. Date: Sep. 19, 2002

(65) Prior Publication Data

US 2004/0072829 A1 Apr. 15, 2004

Related U.S. Application Data

(60) Provisional application No. 60/264,362, filed on Jan. 26, 2001.

(51) Int. Cl.[7] ..................... C07D 403/02; A61K 31/53; A61P 5/30; A61P 35/00
(52) U.S. Cl. ................. 514/241; 544/198; 544/207; 544/209
(58) Field of Search ................. 544/198, 207, 544/209; 514/241

(56) References Cited

U.S. PATENT DOCUMENTS 6,117,996 A * 9/2000 Lowe et al. ................. 544/216

FOREIGN PATENT DOCUMENTS

EP 0 629 622 12/1994
WO 97/10887 3/1997

OTHER PUBLICATIONS

Cecil Textbook of Medicine, edited by Bennet, J.C., and Plum F., 20th edition,vol. 1, 1004–1010, 1996.*
Wolft Manfred E. "Burger's Medicinal Chemistry, 5ed, Part 1", John Wiley & Sons, 1995, pp. 975–977.*
Banker, G.S. et al, "Modern Pharmaceutices, 3ed.", Marcel Dekker, New York. 1996, p. 596.*
West, Anthony R., Solid State Chemistry and its Applications, Wiley, New York, 1988, pp. 358 & 365.*
Jordan V. C., Cancer cell 5(3) 207–13,2000.*

* cited by examiner

Primary Examiner—Venkataraman Balasubramanian
(74) Attorney, Agent, or Firm—John L. Lemanowicz

(57) ABSTRACT

Triazine derivatives of formula (I), which exhibit pharmacological activity at estrogen receptors alpha (ER alpha) and beta (ER beta) are described herein. The described invention also includes compositions and medicaments containing the triazine derivatives as well as processes for the preparation and use of such compounds, compositions and medicaments.

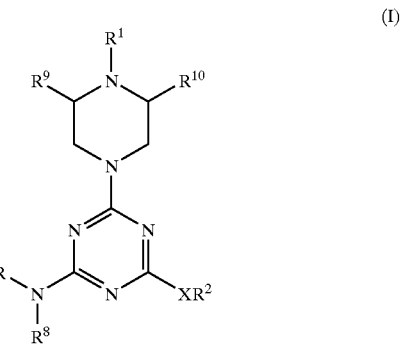

(I)

4 Claims, No Drawings

PIPERAZINYLTRIAZINES AS ESTROGEN RECEPTOR MODULATORS

This application is filed pursuant 35 U.S.C. § 371 as a United States National Phase Application of International Application No. PCT/US02/01758 filed Jan. 23, 2002, which claims priority from 60/264,362 filed Jan. 26, 2001.

BACKGROUND OF THE INVENTION

The present invention relates to triazines, compositions and medicaments containing the same, as well as processes for the preparation and use of such compounds, compositions and medicaments. Such triazines exhibit pharmacological activity at estrogen receptors alpha (ERα) and beta (ERβ).

Estrogens are endocrine regulators in the cellular processes involved in the development and maintenance of the reproductive system. Estrogens have also been shown to have important effects in many non-reproductive tissues such as bone, liver, the cardiovascular system, and the central nervous system. Estrogens exert their effects by binding to an intracellular steroid hormone receptor. After the receptor and bound ligand are translocated to the nucleus of the cell, the complex binds to recognition sites in DNA, which allows for the modulation of certain genes. Certain estrogens have demonstrated the ability to exhibit their biological activity in a "tissue-selective" manner, functioning as estrogen agonists in certain tissues, while acting as estrogen antagonists in other tissues. The term "selective estrogen receptor modulators" (SERMs) has been given to these molecules, examples of which include tamoxifen, raloxifene, lasofoxifene, clomiphene, and nafoxidine. The molecular basis for this tissue selective activity is not completely understood. However, it is thought to involve the ability of the ligand to place the estrogen receptor into different conformational states that allow for differential capabilities in recruiting coactivator and corepressor proteins as well as other important proteins involved in transcriptional regulation (see McDonnell, D. P., "The hmolecular pharmacology of SERMs", Trends Endocrinol. Metab. 1999, 301–311).

Historically, it was thought that estrogens manifested their biological activity through a single estrogen receptor, now termed estrogen receptor alpha (ERα). However, a second subtype of estrogen receptor, termed estrogen receptor beta (ERβ), has recently been discovered (Kuiper G. G. J. M. et. al., WO 9709348; Kuiper, G. G. J. M. et al., "Cloning of a novel estrogen receptor expressed in rat prostate and ovary", Proc. Natl. Acad. Sci. U.S.A. 1996, 5925–5930). ERβ is known to be expressed in humans (Mosselman, S. et. al., "ERβ: identification and characterization of a novel human estrogen receptor", FEBS Lett 1996, 49–53). The discovery of this second subtype of estrogen receptor significantly increased the biological complexity of estrogen signaling and may be responsible for some, but not all, of the tissue-selective actions of the currently available SERMs.

Osteoporosis is characterized by the net loss of bone mass per unit volume. The consequence of this bone loss is failure of the skeleton to provide adequate structural support for the body, resulting in increased incidence of fracture. One of the most common types of osteoporosis is postmenopausal osteoporosis, which is associated with accelerated bone loss subsequent to cessation of menses and declining levels of endogenous estrogen in women. The inverse relationship between densitometric measures of bone mass and fracture risk, for peri- and postmenopausal women in the process of rapid bone loss due to declining levels of estrogen, has been clearly established (Slemenda, C. W. et al., "Predictors of bone mass in perimenopausal women, a prospective study of clinical data using photon absorptiometry", Ann. Intern. Med. 1990, 96–101; Marshall, D. et. al., "Meta-analysis of how well measures of bone mineral density predict occurrence of osteoporotic fractures", Br. Med. J. 1996, 1254–1259). Elderly women currently have a lifetime risk of fractures of ca. 75%, with a 40% risk of hip fracture for white women over age 50 in the United States. The economic burden from osteoporotic fractures is considerable because of the necessity of hospitalization. In addition, although osteoporosis is generally not thought of as life-threatening, the mortality within 4 months of hip fracture is currently 20 to 30%. Current therapies for postmenopausal osteoporosis include estrogen replacement therapy or treatment with other antiresorptive agents such as bisphosphonates or calcitonin. However, patient compliance is low with all these therapies due to undesirable side effects or lack of efficacy.

Cardiovascular disease is the leading cause of death among postmenopausal women. The preponderance of data suggests that estrogen replacement therapy in postmenopausal women reduces the risk of cardiovascular disease, although some studies have reported no beneficial effect on overall mortality (Barrett-Connor, E. et. al., "The potential of SERMs for reducing the risk of coronary heart disease", Trends Endocrinol. Metab. 1999, 320–325). The mechanism(s) by which estrogens exert their beneficial effects on the cardiovascular system are not entirely clear, but are potentially linked to their effects on serum cholesterol and lipoproteins, antioxidant properties, vascular smooth muscle proliferation, and inhibition of arterial cholesterol accumulation (Barrett-Connor, E. et. al., "The potential of SERMs for reducing the risk of coronary heart disease", Trends Endocrinol. Metab. 1999, 320–325; Cosman, F; Lindsay, R. "Selective estrogen receptor modulators: clinical spectrum", Endocrine Rev. 1999, 418–434).

The effects of estrogens on breast tissue, particularly breast cancer, have been well documented. The tissue selective estrogen tamoxifen has conclusively been shown to decrease the risk of recurrent breast cancer, contralateral breast cancer, and mortality as well as increase the disease-free survival in patients with breast cancer at multiple stages of the disease (Cosman, F; Lindsay, R. "Selective estrogen receptor modulators: clinical spectrum". Endocrine Rev. 1999, 418–434). However, the mixed agonist-antagonist profile of tamoxifen is not ideal and may have stimulatory effects on uterine cell populations, leading to a potential increase in uterine cancer. An improved therapy for the treatment of these cancers would be an estrogen with no agonist properties on any reproductive tissues.

The present inventors have now discovered a novel group of triazine compounds, which bind to and modulate estrogen receptor alpha and estrogen receptor beta. These compounds also show good tissue-selective estrogenic activity and are therefore of use in the treatment and/or prophylaxis of postmenopausal osteoporosis, estrogen-dependent breast cancer, and cardiovascular disease. These compounds are also indicated to be of use for the treatment and/or prophylaxis of other diseases including dyslipidemia, relief of menopausal vasomotor symptoms, uterine cancer, prostate cancer, prostate hyperplasia, urinary incontinence, atherosclerosis, uterine fibroid disease, aortic smooth muscle cell proliferation and endometriosis.

BRIEF SUMMARY OF THE INVENTION

In one aspect of the present invention, there is provided a compound of Formula (I):

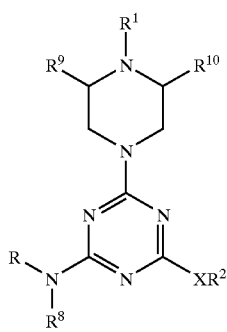

or a salt, solvate, or physiologically functional derivative thereof:
wherein:
X is $NR^3$, S, or O;
R is

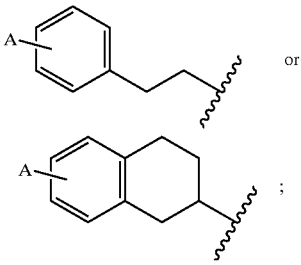

A is —OH
$R^1$ is hydrogen, —$(C_1-C_6)$alkyl, —$C(O)R^4$, —$(CH_2)_mR^4$, —$CR^5$=$CHC(O)R^4$, —$(CH_2)_mC(O)NR^6R^7$, —$CH_2CH$=$CHR^4$, —$C(O)OR^4$, or —$S(O)_2R^4$,
m is 0, 1, 2, or 3;
$R^2$ is —$(CH_2)_n$-$(Z)_p$-$(Z')_q$;
Z is hydrogen, aryl, or $(C_3-C_7)$cycloalkyl;
Z' is aryl;
n is 0, 1, 2, or 3;
p is 0 or 1;
q is 0 or 1;
$R^3$ is hydrogen or —$(C_1-C_6)$alkyl;
$R^4$ is hydrogen, hydroxy, aryl, heteroaryl, heterocyclic, or —$(C_2-C_6)$alkenyl;
$R^5$ is hydrogen or —$(C_1-C_6)$haloalkyl; and
$R^6$, $R^7$, $R^8$, $R^9$, and $R^{10}$ are each independently selected from hydrogen or —$(C_1-C_6)$alkyl.

In a second aspect of the present invention, there is provided a pharmaceutical composition comprising a therapeutically effective amount of a compound of formula I, or a salt, solvate, or a physiologically functional derivative thereof and one or more of pharmaceutically acceptable carriers, diluents and excipients.

In a third aspect of the present invention, there is provided a method of treating a disorder in a mammal, said disorder being mediated by inappropriate estrogen receptor activity, comprising: administering to said mammal a therapeutically effective amount of a compound of formula I or a salt, solvate or a physiologically functional derivative thereof.

In a fourth aspect of the present invention, there is provided a compound of formula I, or a salt, solvate, or a physiologically functional derivative thereof for use in therapy.

In a fifth aspect of the present invention, there is provided the use of a compound of formula I, or a salt, solvate, or a physiologically functional derivative thereof in the preparation of a medicament for use in the treatment of a disorder mediated by inappropriate estrogen receptor activity.

DETAILED DESCRIPTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" refers to a straight or branched chain hydrocarbon having from one to twelve carbon atoms, optionally substituted with substituents selected from the group consisting of $C_1-C_6$ alkyl, $C_1-C_6$ alkoxy, $C_1-C_6$ alkylsulfanyl, $C_1-C_6$ alkylsulfenyl, $C_1-C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or $C_1-C_6$ perfluoroalkyl, multiple degrees of substitution being allowed. Examples of "alkyl" as used herein include, but are not limited to, methyl, ethyl, n-propyl, isopropyl, n-butyl, n-pentyl, isobutyl, and isopropyl, and the like.

As used herein, the term "$C_1-C_6$ alkyl" refers to an alkyl group as defined above containing at least 1, and at most 6, carbon atoms. Examples of branched or straight chained "$C_1-C_6$ alkyl" groups useful in the present invention include, but are not limited to, methyl, ethyl, n-propyl, isopropyl, isobutyl, n-butyl, and t-butyl.

As used herein, the term "alkylene" refers to a straight or branched chain divalent hydrocarbon radical having from one to ten carbon atoms, optionally substituted with substituents selected from the group which includes $C_1-C_6$ alkyl, $C_1-C_6$ alkoxy, $C_1-C_6$ alkylsulfanyl, $C_1-C_6$ alkylsulfenyl, $C_1-C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and $C_1-C_6$ perfluoroalkyl, multiple degrees of substitution being allowed. Examples of "alkylene" as used herein include, but are not limited to, methylene, ethylene, n-propylene, n-butylene, and the like.

As used herein, the term "$C_1-C_3$ alkylene" refers to an alkylene group, as defined above, which contains at least 1, and at most 3, carbon atoms. Examples of "$C_1-C_3$ alkylene" groups useful in the present invention include, but are not limited to, methylene, ethylene, and n-propylene.

As used herein, the term "halogen" refers to fluorine, chlorine, bromine, or iodine.

As used herein, the term "$C_1-C_6$ haloalkyl" refers to an alkyl group as defined above containing at least 1, and at most 6, carbon atoms substituted with at least one halogen, halogen being as defined herein. Examples of branched or straight chained "$C_1$–$C_4$ haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

As used herein, the term "$C_3$–$C_7$ cycloalkyl" refers to a non-aromatic cyclic hydrocarbon ring having from three to seven carbon atoms. Exemplary "$C_3$–$C_7$ cycloalkyl" groups include, but are not limited to, cyclopropyl, cyclobutyl, cyclopentyl, cyclohexyl and cycloheptyl.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include $C_1$–$C_6$ alkyl, $C_1$–$C_6$ haloalkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, halogen, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$–$C_6$ perfluoroalkyl, heteroaryl, or aryl, multiple degrees of substitution being allowed. Examples of "aryl" groups include, but are not limited to, phenyl, 2-naphthyl, 1-naphthyl, biphenyl, as well as substituted derivatives thereof.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of $C_1$–$C_6$ alkyl, $C_1$–$C_6$ alkoxy, $C_1$–$C_6$ haloalkyl, $C_1$–$C_6$ alkylsulfanyl, $C_1$–$C_6$ alkylsulfenyl, $C_1$–$C_6$ alkylsulfonyl, oxo, hydroxy, halogen, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$–$C_6$ perfluoroalkyl, heteroaryl, or aryl, multiple degrees of substitution being allowed. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "heterocyclic" or the term "heterocyelyl refers to a three to twelve-membered non-aromatic heterocyclic ring being saturated or having one or more degrees of unsaturation containing one or more heteroatomic substitutions selected from S, S(O), S(O)$_2$, O, or N, optionally substituted with substituents selected from the group consisting of $C_1$–$C_6$ alkyl, $C_1$–$C_6$ haloalkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, halogen, mercapto, amino optionally substituted by alkyl, carboxy, carbamoyl optionally substituted by alkyl, aminosulfonyl optionally substituted by alkyl, nitro, cyano, halogen, or $C_1$–$C_6$ perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "alkoxy" refers to the group $R_aO$—, where $R_a$ is alkyl as defined above and the terms "$C_1$–$C_6$ alkoxy" and "$C_1$–$C_3$ alkoxy" refer to an alkoxy group as defined herein wherein the alkyl moiety contains at least 1, and at most 6 or 3 carbon atoms respectively.

As used herein the term "aralkoxy" refers to the group $R_bR_aO$—, where $R_a$ is alkyl and $R_b$ is aryl as defined above.

As used herein, the term "alkylsulfanyl" refers to the group $R_aS$—, where $R_a$ is alkyl as defined above and the term "$C_1$–$C_6$ alkylsulfanyl" refers to an alkylsulfanyl group as defined herein wherein the alkyl moiety contains at least 1, and at most 6, carbon atoms.

As used herein, the term "alkylsulfenyl" refers to the group $R_aS(O)$—, where $R_a$ is alkyl as defined above and the term "$C_1$–$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group $R_aS(O)_2$—, where $R_a$ is alkyl as defined above and the term "$C_1$–$C_6$ alkylsulfonyl" refers to an alkylsulfonyl group as defined herein wherein the alkyl moiety contains at least 1, and at most 6, carbon atoms.

As used herein, the term "oxo" refers to the group =O

As used herein, the term "mercapto" refers to the group —SH.

As used herein, the term "carboxy" refers to the group —COOH.

As used herein, the term "cyano" refers to the group —CN.

As used herein the term "cyanoalkyl" refers to the group —$R_a$CN wherein $R_a$ is $C_1$–$C_3$ alkylene as defined above. Exemplary "cyanoalkyl" groups useful in the present invention include, but are not limited to, cyanomethyl, cyanoethyl, and cyanopropyl.

As used herein, the term "aminosulfonyl" refers to the group —S(O)$_2$NH$_2$.

As used herein, the term "carbamoyl" refers to the group —C(O)NH$_2$.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$—.

As used herein, the term "acyl" refers to the group $R_aC(O)$—, where $R_a$ is alkyl, cycloalkyl, or heterocyclyl as defined herein.

As used herein, the term "aroyl" refers to the group $R_aC(O)$—, where $R_a$ is aryl as defined herein.

As used herein, the term "heteroaroyl" refers to the group $R_aC(O)$—, where $R_a$ is heteroaryl as defined herein.

As used herein, the term "alkoxycarbonyl" refers to the group $R_aOC(O)$—, where $R_a$ is alkyl as defined herein.

As used herein, the term "acyloxy" refers to the group $R_aC(O)O$—, where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the group $R_aC(O)O$—, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

The compounds of formula (I) as well as salts, solvates, and physiologically functional derivatives thereof have the ability to crystallize in more than one form, a characteristic, which is known as polymorphism, and it is understood that such polymorphic forms ("polymorphs") are within the scope of formula (I). Polymorphism generally can occur as a response to changes in temperature or pressure or both and can also result from variations in the crystallization process. Polymorphs can be distinguished by various physical characteristics known in the art, such as x-ray diffraction patterns, solubility, and melting point.

As used herein, the term "substituted" refers to substitution with the named substituent or substituents, multiple degrees of substitution being allowed unless otherwise stated.

Certain of the compounds described herein contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted.

In one embodiment, X is NR$^3$ or S. In a preferred embodiment X is NR$^3$. In a more preferred embodiment X is NR$^3$ wherein R$^3$ is hydrogen or methyl.

In one embodiment R is:

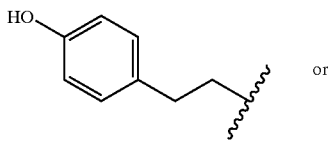 or

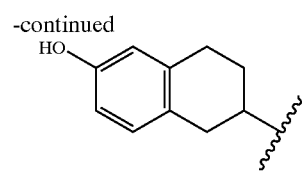

Preferably R is:

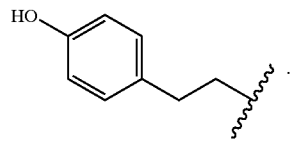

It is understood that R is attached to the indicated nitrogen of Formula (I) through the bond of R having an unfilled valence and being indicated by

The appropriate attachment is further illustrated in the working examples recited below.

In one embodiment, R$^1$ is hydrogen, —(C$_1$–C$_6$) alkyl, or —(CH$_2$)$_m$R$^4$, wherein m is 1 or 2. In a preferred embodiment, R$^1$ is hydrogen or —(C$_1$–C$_6$) alkyl. In a more preferred embodiment, R$^1$ is hydrogen or methyl.

In one embodiment, R$^2$ is —(CH$_2$)$_n$-(Z)$_p$-(Z')$_q$, wherein n is 0, 1, 2, or 3; p is 0; q is 1; Z' is aryl, optionally substituted with one or more halogen atoms, C$_{1-3}$ alkoxy, or cyano. In a preferred embodiment, R$^2$ is —(CH$_2$)$_n$-(Z)$_p$-(Z')$_q$, wherein n is 0, 1, 2, or 3; p is 0; q is 1; Z' is phenyl, optionally substituted with one or more halogen atoms, C$_{1-3}$ alkoxy, or cyano.

In one embodiment, X is NR$^3$ or S, wherein R$^3$ is H or methyl; R is:

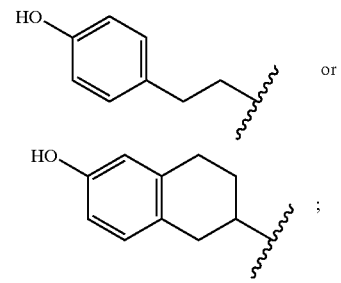

R$^1$ is hydrogen, —(C$_1$–C$_6$) alkyl, or —(CH$_2$)$_m$R$^4$, wherein m is 1 or 2; R$^2$ is —(CH$_2$)$_n$-(Z)$_p$-(Z')$_q$, wherein n is 0, 1, 2, or 3; p is 0, q is 1; Z' is aryl, optionally substituted with one or more halogen atoms, C$_{1-3}$ alkoxy, or cyano; R$^4$ is H; and R$^5$, R$^6$, R$^7$, R$^8$, R$^9$, and R$^{10}$, are independently selected from hydrogen or methyl.

In a preferred embodiment, X is NR$^3$, wherein R$^3$ is H or methyl; R is:

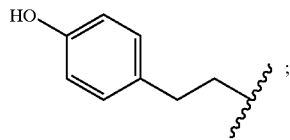

R$^1$ is hydrogen or methyl; R$^2$ is —(CH$_2$)$_n$-(Z)$_p$-(Z')$_q$, wherein n is 0, 1, 2, or 3; p is 0; q is 1; Z' is phenyl, optionally substituted with one or more halogen atoms, C$_{1-3}$ alkoxy, or cyano; R$^4$ is H; and R$^5$, R$^6$, R$^7$, R$^8$, R$^9$, and R$^{10}$, are independently selected from hydrogen or methyl.

Specific examples of compounds of the present invention include the following:

4-(2-{[4-[[3-(4-chlorophenyl)propyl](methyl)amino]-6-(1-piperazinyl)-1,3,5-triazin-2-yl]amino}ethyl)phenol;

4-(2-{[4-(methyl{[(1S*,2R*)-2-phenylcyclopropyl]methyl}amino)-6-(1-piperazinyl)-1,3,5-triazin-2-yl]amino}ethyl)phenol;

4-[2-({4-[[3-(4-chlorophenyl)propyl](methyl)amino]-6-[4-(3-methoxybenzoyl)-1-piperazinyl]-1,3,5-triazin-2-yl}amino)ethyl]phenol;

4-[2-({4-[[3-(4-chlorophenyl)propyl](methyl)amino]-6-[4-(2-pyridinylcarbonyl)-1-piperazinyl]-1,3,5-triazin-2-yl}amino)ethyl]phenol;

4-[2-({4-[[3-(4-chlorophenyl)propyl](methyl)amino]-6-[4-(2-pyridinylmethyl)-1-piperazinyl]-1,3,5-triazin-2-yl}amino)ethyl]phenol;

4-[2-({4-[[3-(4-chlorophenyl)propyl](methyl)amino]-6-[4-(3-pyridinylmethyl)-1-piperazinyl]-1,3,5-triazin-2-yl}amino)ethyl]phenol;

4-{2-[(4-[[3-(4-chlorophenyl)propyl](methyl)amino]-6-{4-[(2-methyl-1,3-thiazol-4-yl)methyl]-1-piperazinyl}-1,3,5-triazin-2-yl)amino]ethyl}phenol;

(2E)-3-[4-(4-[[3-(4-chlorophenyl)propyl](methyl)amino]-6-{[2-(4-hydroxyphenyl)ethyl]amino}-1,3,5-triazin-2-yl)-1-piperazinyl]-4,4,4-trifluoro-1-phenyl-2-buten-1-one;

3-[4-(4-[[3-(4-chlorophenyl)propyl](methyl)amino]-6-{[2-(4-hydroxyphenyl)ethyl]amino}-1,3,5-triazin-2-yl)-1-piperazinyl]-N,N-dimethylpropanamide;

6-({4-(4-methyl-1-piperazinyl)-6-[(3-phenylpropyl)sulfanyl]-1,3,5-triazin-2-yl}amino)-5,6,7,8-tetrahydro-2-naphthalenol;

4-(2-{[4-{[3-(4-chlorophenyl)propyl]sulfanyl}-6-(1-piperazinyl)-1,3,5-triazin-2-yl]amino}ethyl)phenol;

4-[2-({4-(4-allyl-1-piperazinyl)-6-[[3-(4-chlorophenyl)propyl](methyl)amino]-1,3,5-triazin-2-yl}amino)ethyl]phenol;

4-{2-[(4-[[3-(4-chlorophenyl)propyl](methyl)amino]-6-{4-[(2E)-3-phenyl-2-propenyl]-1-piperazinyl}-1,3,5-triazin-2-yl)amino]ethyl}phenol;

4-{2-[[4-[[3-(4-chlorophenyl)propyl](methyl)amino]-6-(1-piperazinyl)-1,3,5-triazin-2-yl](methyl)amino]ethyl}phenol;

4-(2-{[4-[[3-(4-chlorophenyl)propyl](methyl)amino]-6-(4-methyl-1-piperazinyl)-1,3,5-triazin-2-yl](methyl)amino}ethyl)phenol;

4-(2-{[4-[[3-(4-chlorophenyl)propyl](methyl)amino]-6-(3,5-cis-dimethyl-1-piperazinyl)-1,3,5-triazin-2-yl](methyl)amino}ethyl)phenol;

4-{2-[{4-[[3-(4-chlorophenyl)propyl](methyl)amino]-6-[4-(2-hydroxyethyl)-1-piperazinyl]-1,3,5-triazin-2-yl}(methyl)amino]ethyl}phenol;

4-(2-{[4-[[3-(4-fluorophenyl)propyl](methyl)amino]-6-(1-piperazinyl)-1,3,5-triazin-2-yl]amino}ethyl)phenol;

4-(2-{[4-[[3-(4-fluorophenyl)propyl](methyl)amino]-6-(1-piperazinyl)-1,3,5-triazin-2-yl]methylamino}ethyl)phenol;

4-(2-{[4-[[3-(4-fluorophenyl)propyl](methyl)amino]-6-(4-methyl-1-piperazinyl)-1,3,5-triazin-2-yl]methylamino}ethyl)phenol;

4-(2-{[4-[[3-(3,4-difluorophenyl)propyl](methyl)amino]-6-(1-piperazinyl)-1,3,5-triazin-2-yl]methylamino}ethyl)phenol;

4-(2-{methyl[4-(methyl{3-[4-(trifluoromethyl)phenyl]propyl}amino)-6-(1-piperazinyl)-1,3,5-triazin-2-yl]amino}ethyl)phenol;

4-(2-{[4-[[3-(2,4-dichlorophenyl)propyl](methyl)amino]-6-(1-piperazinyl)-1,3,5-triazin-2-yl]methylamino}ethyl)phenol; and 4-[2-({4-[[3-(4-chlorophenyl)propyl](methyl)amino]-6-[4-(2-hydroxyethyl)-1-piperazinyl]-1,3,5-triazin-2-yl}amino)ethyl]phenol;

or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I) depending on the condition being treated, the route of administration and the age, weight and condition of the patient. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide—phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. An effective amount of a salt or solvate, or physiologically functional derivative thereof, may be determined as a proportion of the effective amount of the compound of formula (I) per se.

The compounds of formula (I) and salts, solvates and physiological functional derivatives thereof, have activity at estrogen receptors alpha (ERα) and beta (ERβ) thereby, it is believed, enabling them to modulate diseases and conditions associated with estrogen or the loss of estrogen, including postmenopausal osteoporosis, breast cancer, uterine cancer, prostate cancer, cardiovascular disease, postmenopausal vasomotor symptoms, cognitive disorders, urinary incontinence, uterine fibroid disease, endometriosis, and prostatic hyperplasia. Accordingly, the present invention is directed to methods of regulating, modulating, or inhibiting estrogen receptors for the prevention and/or treatment of disorders related to unregulated estrogen receptor activity.

The present invention thus also provides compounds of formula (I) and pharmaceutically acceptable salts or solvates thereof, or physiologically functional derivatives thereof, for use in medical therapy, and particularly in the treatment of disorders mediated by inappropriate estrogen receptor activity.

The inappropriate estrogen receptor activity referred to herein is any estrogen receptor activity that deviates from the normal estrogen receptor activity expected in a particular mammalian subject. Inappropriate estrogen receptor activity may take the form of, for instance, an abnormal increase or decrease in activity, or an aberration in the timing and or control of estrogen receptor activity.

A further aspect of the invention provides a method of treatment of a mammal suffering from a disorder mediated by inappropriate estrogen receptor activity, which includes administering to said subject an effective amount of a compound of formula (I) or a pharmaceutically acceptable salt, solvate, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by inappropriate estrogen receptor activity.

The mammal requiring treatment with a compound of the present invention is typically a human being.

The compounds of this invention may be made by a variety of methods, including standard chemistry. Any previously defined variable will continue to have the previously defined meaning unless otherwise indicated. Illustrative synthetic methods are set out below for specific compounds of the invention in the working examples following.

Compounds of general formula (I) may be prepared by methods known in the art of organic synthesis as set forth in part by the following working example synthesis. In all of the working examples described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley Et Sons). These groups are removed at a convenient stage of the compound synthesis using methods that are readily apparent to those skilled in the art. The selection of processes as well as the reaction conditions and order of their execution shall be consistent with the preparation of compounds of Formula I. Those skilled in the art will recognize if a stereocenter exists in compounds of Formula I. Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-interscience, 1994).

Certain embodiments of the present invention will now be illustrated by way of working examples. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230–400 mesh, Merck). Optical rotations were obtained using a Perkin Elmer Model 241 Polarimeter. Melting points were determined using a Mel-Temp II apparatus and are uncorrected.

g (grams); mg (milligrams);
L (liters); mL (milliliters);
μL (microliters); psi (pounds per square inch);
M (molar); mM (millimolar);
i. v. (intravenous); Hz (Hertz);
MHz (megahertz); mol (moles);
mmol (millimoles); RT (room temperature);
min (minutes); h (hours);
mp (melting point); TLC (thin layer chromatography);
T$_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); (CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid; EDC (ethylcarbodiimide hydrochloride);
BOC (tert-butyloxycarbonyl); FMOC (9-fluorenylmethoxycarbonyl);
(dicyclohexylcarbodiimide); CBZ (benzyloxycarbonyl);
Ac (acetyl); atm (atmosphere);
HPLC (high pressure liquid chromatography);
BOP (bis(2-oxo-3-oxazolidinyl)phosphinic chloride);
TBAF (tetra-n-butylammonium fluoride);

Preparation of Intermediates

Intermediate 1: tert-butyl-4-(4,6-dichloro-1,3,5-triazin-2-yl)-1-piperazinecarboxylate.

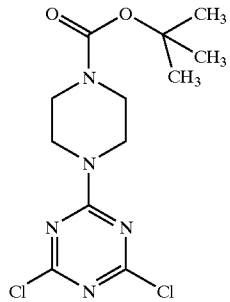

A stirred solution of 5.3 g (29.0 mmol) of cyanuric chloride in 200 mL of DCM was cooled to −10° C. A solution of 5.3 g (29.0 mmol, 1.0 equiv.) of N-BOC piperazine and 6.2 g (29.0 mmo, 1.0 equiv.) of Proton Sponge® in 40 mL of DCM was then added dropwise over 20 min. to the cyanuric chloride solution. The resulting mixture was allowed to warm to RT and stirred 2 h. The reaction mixture was quenched by pouring into 150 mL of a 5% aqueous citric acid solution and extracted with DCM (2×100 mL). The organic layers were combined, dried (MgSO$_4$), and concentrated in vacuo. Purification of the residue by silica gel flash column chromatography eluting with hexanes/EtOAc 3:1 afforded 8.6 g (85%) of the title compound as a white solid: $^1$H NMR (CDCl$_3$, 400 MHz) δ 3.86 (m, 4H), 3.49 (m, 4H), 1.42 (s, 9H); low resolution MS (ES$^+$) m/e 335 (MH$^+$); TLC (hexanes/EtOAc 20:1) R$_f$=0.10.

Intermediate 2: tert-butyl-4-{4-chloro-6-[[3-(4-chlorophenyl)propyl](methyl)amino]-1,3,5-triazin-2-yl}-1-piperazinecarboxylate.

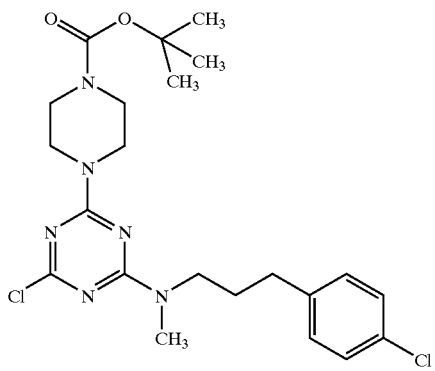

A stirred solution of 1.2 g (3.6 mmol) of Intermediate 1 in 30 mL of THF was cooled to 0° C. A solution of 555 mg (4.3 mmol, 1.2 equiv.) of N,N-diisopropylethylamine and 735 mg (4.0 mmol, 1.1 equiv.) of (Intermediate 4) in 10 mL of THF was added dropwise over 5 min. The resulting mixture was stirred at 0° C. for 5 min after the addition was complete then allowed to warm to RT and stirred 16 h. The reaction mixture was then poured into brine (100 mL) and extracted with EtOAc (2×100 mL). The organic layers were combined, dried (MgSO$_4$), and concentrated in vacuo. Purification of the residue by silica gel chromatography eluting with hexanes/EtOAc 4:1 afforded 1.7 g (100%) of the title compound as a clear oil: $^1$H NMR (CDCl$_3$, 400 MHz) δ 7.24 (m, 2H), 7.08 (m, 2H), 3.78 (m, 2H), 3.49 (m, 8H), 3.12 (s, 3H), 2.80 (m, 2H), 1.94 (m, 2H), 1.42 (s, 9H); low resolution MS (ES$^+$) m/e 583 (MH$^+$); TLC (hexanes/EtOAc 2:1) R$_f$=0.50.

Intermediate 3: tert-butyl 4-(4-[[3-(4-chlorophenyl)propyl](methyl)amino]-6-{[2-(4-hydroxyphenyl)ethyl]amino}-1,3,5-triazin-2-yl)-1-piperazinecarboxylate.

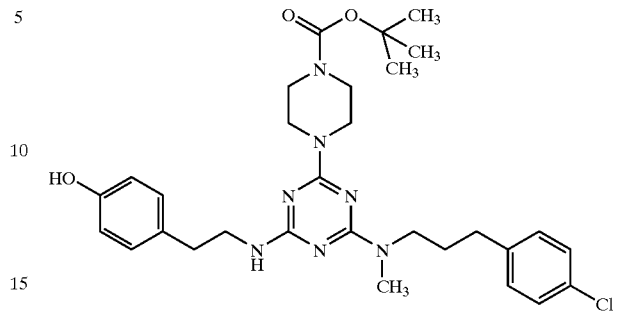

A stirred solution of 1.7 g (3.5 mmol) of Intermediate 2 in 50 mL of CH$_3$CN at RT was treated with a solution of 1.1 g (7.7 mmol, 2.2 equiv.) of tyramine in 10 mL of DMF. The resulting solution was heated to 85° C. for 6 h and then cooled to RT. The reaction was poured into 150 mL of a 1:1 mixture of EtOAc and ether and extracted with brine (1×150 mL). The organic layer was separated, dried (MgSO$_4$), and concentrated in vacuo. Purification of the residue by silica gel chromatography eluting with hexanes/EtOAc 2:1 afforded 1.4 g (70%) of the title compound as a clear light yellow oil: $^1$H NMR (CDCl$_3$, 400 MHz) δ 7.22 (d, 2H, J=8.0), 7.08 (d, 2H, J=8.0), 7.01 (d, 2H, J=8.3, 6.65 (d, 2H, J=8.3), 4.82 (s, br, 1H), 3.88–3.41 (m, 10H), 3.05 (s, 3H), 2.77 (t, 2H, J=6.8), 2.58 (m, 2H), 1.86 (m, 2H), 1.65 (m, 2H), 1.48 (s, 9H); TLC (hexanes/EtOAc 2:1) R$_f$=0.15.

Intermediate 4: N-[3-(4-chlorophenyl)propyl]-N-methylamine.

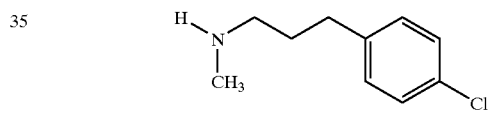

A stirred solution of 3.0 g (16.2 mmol) of 4-chlorophenylpropionic acid in 20 mL of DCM was reacted with 3.1 g (19.4 mmol, 1.2 equiv.) of 1,1'-carbonyldiimidazole by addition of 500 mg portions over a 15 min period, during which time significant evolution of CO was observed. The resulting solution was stirred 90 min at RT, then cooled to 0° C. and treated with 8 mL of a cold (0° C.) 40% aqueous solution of methylamine. The resulting mixture was allowed to warm to RT and stirred vigorously for 14 h. The reaction mixture was then acidified to a pH of 1 by careful addition of conc. HCl, diluted with 70 mL of chloroform and extracted with H$_2$O (1×100 mL). The organic layer was separated, dried (MgSO$_4$), and concentrated in vacuo to afford 3.1 g of a white solid. This material was immediately dissolved in 80 mL of THF, and 19.4 mL of a 1.0 M solution of LiAlH$_4$ in THF was added dropwise over 10 min. After the addition was complete, the resulting solution was stirred 10 min at RT and then was heated to 60° C. for 6 h. The reaction mixture was then cooled to 0° C. and the reaction was quenched by careful addition of 0.76 mL of H$_2$O, followed by 0.76 mL of 15% NaOH and then 2.7 mL of H$_2$O. The resulting slurry was stirred vigorously for 10 min. and then filtered through a pad of Celite to remove the salts. The salts were isolated, triturated with EtOAc, and refiltered through a pad of Celite. The filtrates were combined, dried (MgSO$_4$), and concentrated in vacuo to afford 3.01 g (98%) of the title compound as a clear yellow oil, which was used without further purification: $^1$H NMR (CDCl$_3$, 400 MHz) δ 7.27 (d, 2H, J=8.4), 7.14 (d, 2H, J=8.4), 2.53 (m, 4H), 2.45 (s, 3H), 1.81 (m, 2H), 1.57 (s, br, 1H); TLC (chloroform/MeOH 9:1) $R_f$=0.10.

Intermediate 5: N-[3-(fluorophenyl)propyl]-N-methylamine.

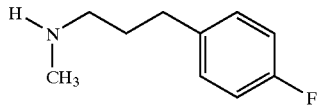

The title compound was prepared in 29% yield via the procedure outlined for the preparation of intermediate 4 using 3-(4-fluorophenyl)propionic acid to give a colorless oil: $^1$H NMR (CDCl$_3$, 400 MHz) δ 7.13 (m, 2H), 6.96 (d, 2H, J=8.8), 2.61 (m, 4H), 2.43 (s, 3H), 1.79 (m, 2H), 1.55 (s, br, 1H); low-resolution MS (ES$^+$) m/e 168 (MH$^+$).

Intermediate 6: N-[3-(3,4-difluorophenyl)propyl]-N-methylamine.

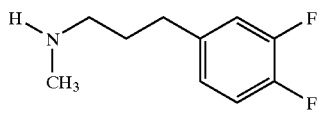

The title compound was prepared in 56% yield via the procedure outlined for the preparation of Intermediate 4 using 3-(3,4-difluorophenyl)propionic acid to give a crude oil, which was distilled under vacuum: $^1$H NMR (CDCl$_3$, 400 MHz) δ 7.08–6.90 (m, 2H), 6.89 (s, br, 1H), 2.59 (m, 4H), 2.43 (s, 3H), 1.78 (m, 2H), 1.59(s, br, 1H); GCMS (DB-5, 30 m×0.25 mm×0.25□m; 100° C.–300° C., initial hold 1 min; ramp rate 25° C./min for 8 min, final hold 1 min; total 10 min) t$_r$=3.77 min, 97.5% purity; MS m/e 185 (M$^+$).

Intermediate 7: N-[3-(4-trifluoromethylphenyl)propyl]-N-methylamine

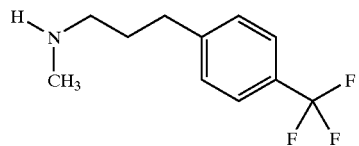

The title compound was prepared in 90% yield via the procedure outlined for Intermediate 4 using 3-(4-trifluoromethylphenyl)propionic acid to give a colorless oil: $^1$H NMR (CDCl$_3$, 400 MHz) δ 7.53 (d, 2H, J=8.0), 7.29 (d, 2H, J=8.0), 2.71 (m, 2H), 2.61 (m, 2H), 2.44 (s, 3H), 1.83 (m, 2H), 1.55 (s, br, 1H); GCMS (DB-5, 30 m×0.25 mm×0.25 μm; 100° C.–300° C., initial hold 1 min; ramp rate 25° C./min for 8 min, final hold 1 min; total 10 min) t$_r$=3.74 min, 94.7% purity; MS m/e 217(M$^+$).

Intermediate 8: N-[3-(2,4-dichlorophenyl)propyl]-N-methylamine.

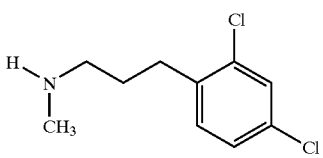

The title compound was prepared in 38% yield via the procedure outlined for Intermediate 4 using 2,4-dichloropropionic acid to give a crude oil, which was distilled under vacuum: $^1$H NMR (CDCl$_3$, 400 MHz) δ 7.35 (s, br, 1H), 7.16 (s, br, 2H), 2.74 (m, 2H), 2.63 (m, 2H), 2.44 (s, 3H), 1.79 (m, 2H), 1.69(s, br, 1H); GCMS (DB-5, 30 m×0.25 mm×0.25 μm; 100° C.–300° C., initial hold 1 min; ramp rate 25° C./min for 8 min, final hold 1 min; total 10 min) t$_r$=5.48 min, 89.9% purity; MS m/e 216 (M$^+$), 182.

Intermediate 9: N-methyl-N-{[(1S*,2R*)-2-phenylcyclopropyl]methyl}amine.

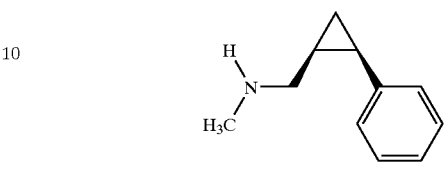

A stirred solution of 850 mg (4.8 mmol) of N-methyl-2-phenylcyclopropanecarboxamide (prepared via literature method; see Borne, F. et. al., *J. Med.Chem.* 1977, 20, 771 and *Org. Synth*, Coll. Vol. VI, 913) in 20 mL of THF was treated dropwise with 5.8 mL (5.8 mmol, 1.2 equiv) of a 1.0 M solution of LiAlH$_4$ in THF. The resulting solution was stirred 20 min after addition was complete, then heated to 55° C. for 15 h. The reaction mixture was then cooled to 0° C. and quenched by careful addition of 0.23 mL of H$_2$O, followed by 0.23 mL of 15% NaOH and then 0.68 mL of H$_2$O. The resulting slurry was stirred vigorously for 10 min. and then filtered through a pad of Celite to remove the salts. The salts were isolated, triturated with EtOAc, and refiltered through a pad of Celite. The filtrates were combined, dried (MgSO$_4$), and concentrated in vacuo to afford 745 mg (95%) of the title compound as a clear light yellow oil, which was used without further purification: $^1$H NMR (CDCl$_3$, 400 MHz) δ 7.23 (m, 5H), 2.33 (m, 1H), 2.22 (s, 3H), 2.19 (m, 1H), 2.02 (m, 2H), 1.36 (dd, 1H, J=8.4, 14.4), 1.01 (m, 1H), 0.82 (dd, 1H, J=5.5, 11.2); TLC (chloroform/MeOH 9:1) $R_f$=0.05.

Intermediate 10: 4-[2-{methylamino}ethyl]phenol hydrobromide

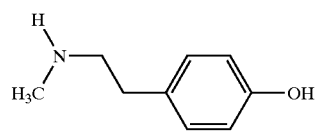

A stirred solution of 7.72 g (46.7 mmol) of N-methyl-β-(4-methoxyphenyl)-ethylamine (prepared in 93% yield via literature method; see Kirkwood, S. et. al., *J. Am. Chem. Soc.* 1950, 72, 2522–2524) in 18 mL of DCM was treated dropwise with 56 mL of a 1.0M solution of BBr$_3$ in DCM at −10 to 0° C. The resulting solution was stirred 20 min. after addition was complete, then stirred at RT for 15 h. The reaction mixture was then cooled to 0° C. and quenched by careful addition of 20 mL of MeOH, stirred vigorously for 30 min. and then concentrated in vacuo. The residual solids were triturated with DCM (2×40 ml) and light brown solids were filtered. The solids were again triturated with acetone/DCM, and filtered to afford 7.12 g (66%) of the title compound as a white solid, which was used without further purification: $^1$H NMR (DMSO-d$_6$, 400 MHz) δ 9.33 (s, 1H), 8.43 (s, br, 2H) 7.04 (d, 2H, J=8), 6.71 (d, 2 H J=8), 3.07 (m, 2H), 2.28 (m, 2H), 2.56 (s, 3H); low-resolution MS (ES$^+$) m/e 152.2(MH$^+$).

Intermediate 11: N-benzyl-6-methyl-1,2,3,4-tetrahydro-2-naphthalenamine

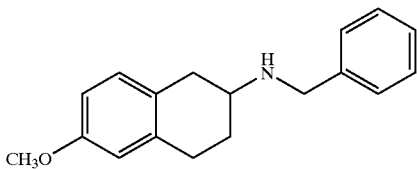

Triacetoxysodium borohydride (1.673 g, 7.89 mmol) and acetic acid (0.32 mL 5.64 mmol) were added to a solution of 6-methoxy-β-tetralone (0.993 g, 5.64 mmol) and benzylamine (0.62 my 5.64 mmol) in $CH_2Cl_2$ (20 mL). The resulting solution was stirred at RT for 8 h. The reaction was diluted with $CH_2Cl_2$ (20 mL) and washed with 1N NaOH (3×60 mL). The organic layer was dried over anhydrous sodium sulfate, filtered, and concentrated to a brown oil which was used without further purification: $^1$H NMR ($CDCl_3$, 300 MHz) δ 7.39–7.25 (m, 5H), 6.99 (d, 1H, J=8), 6.69 (dd, 1H, J=3, 8), 6.62 (d, 1H, J=3), 3.92 (s, 2H), 3.77 (s, 3H), 3.00 (m, 2H), 2.92–2.74 (m, 2H), 2.63 (m, 1H), 2.10 (m, 1H), 1.68 (m, 1H). TLC (10% MeOH/EtOAc): $R_f$=0.48.

Intermediate 12: 2,4-dichloro-6-[(3-phenylpropyl)sulfanyl]-1,3,5-triazine.

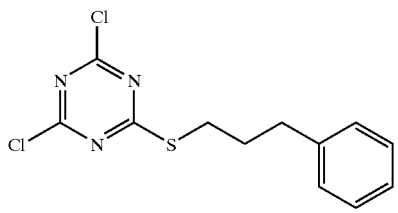

A slurry of cyanuric chloride (3.065 g, 16.62 mmol) in $CH_2Cl_2$ (40 mL) was cooled to 0° C. and a solution of 3-phenylpropylthiol (2.5 mL, 16.62 mmol) and N,N'-diisopropyl-N-ethylamine (2.9 mL, 16.62 mmol) in $CH_2Cl_2$ (10 mL) was added dropwise. The mixture was stirred for 2 h, diluted with 10% aqueous citric acid (100 mL) and extracted with $CH_2Cl_2$. The extracts were dried over magnesium sulfate, filtered and concentrated to give a yellow oil which solidified upon standing (4.89 g, 98%). The material was used without further purification: $^1$H NMR ($CDCl_3$, 300 MHz) δ 7.34–7.16 (m, 5H), 3.18 (t, 2H, J=7), 2.78 (t, 2H, J=7), 2.09 (q, 2H, J=8). TLC (10% EtOAc/hexanes): $R_f$=0.51.

Intermediate 13: 2,4-dichloro-6-{[3-(4-chlorophenyl)propyl]methylamino}-1,3,5-triazine

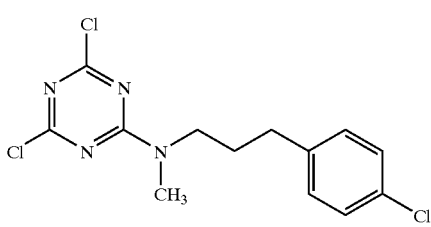

A stirred solution of 919 mg (5.0 mmol) of cyanuric chloride in 50 mL of DCM was cooled to −45° C. A solution of Intermediate 4 (919 mg, 5. mmol) and 660 mg (5.0 mmol, 1.0 equiv.) of N,N'-diisopropyl-N-ethylamine in 40 mL of DCM was then added dropwise over 20 min. to the cyanuric chloride solution. The resulting mixture was allowed to warm to RT and stirred 1 h. The reaction mixture was diluted with DCM (40 mL) and washed with 10% aqueous citric acid solution (2×40 ml). The organic layers were combined, dried ($MgSO_4$), and concentrated in vacuo. Purification of the residue by silica gel flash column chromatography eluting with hexanes/DCM 3:5 afforded 950 mg (89%) of the title compound as a white solid: $^1$H NMR ($CDCl_3$, 400 MHz) δ 7.27 (d, 2H, J=8.0), 7.13 (d, 2H, J=8.0), 3.65 (t, 2 H J=7.2), 3.16 (s, 3H), 2.64 (t, 2H, J=7.6), 1.94 (m, 2H); TLC (40% $CH_2Cl_2$/hexanes): $R_f$=0.35.

Intermediate 14: 6-amino-5,6,7,8-tetrahydro-2-naphthaenol

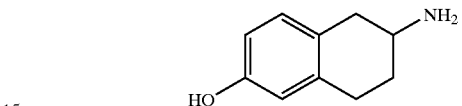

A mixture of Intermediate 11 (1.506 g, 5.64 mmol) and 10% Pd/C (1.500 g) in 1:1 ethanol/THF (60 mL) was shaken on a Parr hydrogenator at 50 psi for 8 h. The reaction mixture was diluted with EtOAc (50 mL) and filtered through Celite. The filtrate was concentrated to give the debenzylated amine (0.990 g, 99%) as a black oil. The material was dissolved in 48% aqueous HBr (40 mL) and refluxed for 8 h. The solvent was then removed under reduced pressure and the resulting yellow oil was triturated (ether/ethanol) to give the title compound as a pale yellow solid (0.984 g, 74%). $^1$H NMR (DMSO-$d_6$, 300 MHz) δ 9.14 (bs, 1H), 7.95 (bs, 3H), 6.89 (d, 1H, J=8), 6.53 (dd, 1H, J=2, 8), 6.47 (d, 1H, J=2), 3.39 (bs, 1H), 2.93 (dd, 1H, J=5, 16), 2.73 (dd, 2 H J=5, 8), 2.62 (dd, 1H, J=10, 15), 2.09–1.95 (m, 1H), 1.64 (m, 1H).

Intermediate 15: 3-(4-chlorophenyl)-1-propanol

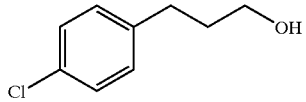

A 1 M solution of borane-THF complex (60 mL) was added dropwise to a solution of 4-chlorophenylpropionic acid (10.05 g, 54.44 mmol) in THF (50 mL) cooled to 0° C. The reaction was stirred for 4 h, diluted with 0.1 N HCl (200 mL) and extracted with EtOAc. The organic extracts were dried over magnesium sulfate, filtered and concentrated. The resulting oil was purified by flash chromatography on silica gel (50% EtOAc/hexanes) to give the title compound (8.95 g, 96%) as a colorless oil. $^1$H NMR ($CDCl_3$, 300 MHz) δ 7.28 (d, 2H, J=8), 7.16 (d, 2H, J=8), 3.70 (t, 2H, J=6), 2.72 (t, 2H, J=8), 1.90 (dt, 2H, J=6, 15), 1.36 (s, 1H). TLC (5% MeOH/$CHCl_3$): $R_f$=0.37.

Intermediate 16: 3-(4-chlorophenyl)propyl methanesulfonate

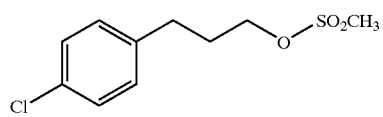

Methanesulfonyl chloride (4.53 mL, 58.5 mmol) was added dropwise to a solution of triethylamine (8.15 mL, 58.5 mmol) and Intermediate 15 (8.319 g, 48.75 mmol) in THF (100 mL) at 0° C. The reaction was stirred at 0° C. for 1 h, then warmed to RT for 3 h, and then diluted with cold water (80 mL). The organic layer was extracted with ether, dried over magnesium sulfate, and concentrated to afford the title compound as a colorless oil (8.13 g, 67%) which was used without further purification: $^1$H NMR ($CDCl_3$, 300 MHz) δ 7.27 (d, 2H, J=8), 7.12 (d, 2H, J=8), 4.22 (t, 2H, J=6), 3.00

(s, 3H), 2.73 (t, 2H, J=6), 2.05 (dt, 2H, J=6, 15 Hz); TLC (50% EtOAc/hexanes): R$_f$=0.52.
Intermediate 17: S-[3-(4-chlorophenyl)propyl] ethanethioate.

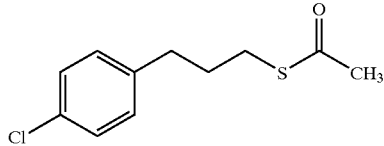

Potassium thioacetate (3.65 g, 31.9 mmol) was added to a solution of Intermediate 16 (1.51 g, 6.07 mmol) in DMF (35 mL). The slurry was stirred 8 h at RT, diluted with EtOAc (100 mL), and washed with brine (3×50 mL). The organic layer was dried over magnesium sulfate, filtered and concentrated. The resulting brown oil was purified by flash chromatography on silica gel (5% EtOAc/hexanes) to give the title compound (1.248 g, 90%) as a light yellow oil: $^1$H NMR (CDCl$_3$, 300 MHz) δ 7.24 (d, 2H, J=8), 7.10 (d, 2H, J=8), 2.86 (t, 2H, J=7), 2.65 (t, 2H, J=8 Hz), 2.33 (s, 3H), 1.87 (q, 2H, J=7); TLC (20% EtOAc/hexanes): R$_f$=0.62.
Intermediate 18: 2,4-dichloro-6-{[3-(4-chlorophenyl)propyl]sulfanyl}-1,3,5-triazine

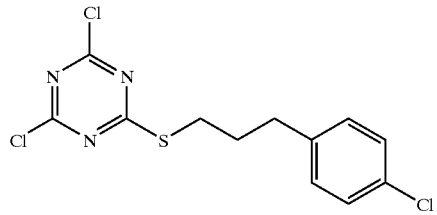

1 N NaOH (6 mL) was added to a degassed solution of Intermediate 17 (1.248 g, 5.46 mmol) in methanol (55 mL). The reaction was stirred at RT for 2 h, diluted with H$_2$O (200 mL), and extracted with EtOAc. The organic extracts were dried over magnesium sulfate, filtered, and concentrated to give the crude thiol as a yellow oil (0.979 g, 96%) which was used without further purification. TLC (10% CH$_2$Cl$_2$/hexanes): R$_f$=0.41. A slurry of cyanuric chloride (0.955 g, 5.18 mmol), in 20 mL of CH$_2$Cl$_2$ was cooled to 0° C. and a solution of the crude thiol and N,N'-diisopropyl-N-ethylamine (0.90 mL, 5.18 mmol) in CH$_2$Cl$_2$ (10 mL) was added dropwise. The mixture was stirred for 2 h, diluted with 100% aqueous citric acid (100 mL) and extracted with CH$_2$Cl$_2$. The resulting residue was purified by flash chromatography on silica gel (40% CH$_2$Cl$_2$/hexanes) to give the title compound as a light yellow solid (1.255 g, 72%): $^1$H NMR (CDCl$_3$, 300 MHz) δ 7.24 (d, 2H, J=8), 7.10 (d, 2H, J=8), 3.13 (t, 2H, J=7), 2.72 (t, 2H, J=7), 2.03 (q, 2H, J=7); TLC (40% CH$_2$Cl$_2$/hexanes): R$_f$=0.31.
Intermediate 19: 4-{2-[(4-chloro-6-{[3-(4-chlorophenyl)propyl]sulfanyl}-1,3,5-triazin-2-yl)amino]ethyl}phenol

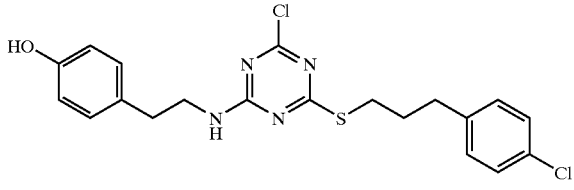

A solution of tyramine (0.514 g, 3.75 mmol) and DIEA (0.65 mL, 3.75 mmol) in ethanol (10 mL) was added dropwise to a solution of Intermediate 18 (1.255 g, 3.75 mmol) in acetonitrile (10 mL). It was stirred at RT for 8 h. The solvent was removed under reduced pressure and the resulting residue was diluted with EtOAc (50 mL) and washed with 10% aqueous citric acid (3×40 mL). The organic layer was dried over magnesium sulfate, filtered, and concentrated to give a residue which was purified by flash chromatography on silica gel (30% EtOAc/hexanes) to give the title compound (1.046 g, 64%) as a white solid: TLC (30% EtOAc/hexanes): R$_f$=0.33; Low resolution MS (ES$^+$) m/e 435 (MH$^+$).
Intermediate 20. 4-{2-[(4-chloro-6-{[3-(4-chlorophenyl)propyl]methylamino}-1,3,5-triazin-2-yl)methylamino]ethyl}phenol

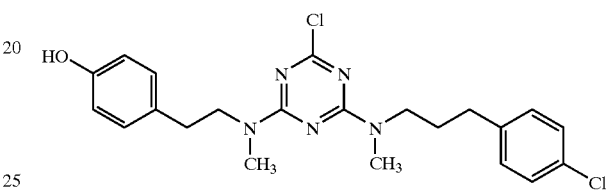

A solution of Intermediate 10 (1.044 g, 4.43 mmol) and DIEA (1.17 g, 9.0 mmol) in DMF (10 mL) was added dropwise to a solution of Intermediate 13 (1.468 g, 4.43 mmol) in DMF (10 mL). The resulting solution was stirred at RT for 2 h. The solvent was removed under reduced pressure and the resulting residue was diluted with EtOAc (80 mL) and washed with 10% aqueous citric acid (3×40 mL). The organic layer was dried over sodium sulfate and concentrated to give the title compound (1.970 g, 98%) as a white solid which was used without further purification: $^1$H NMR (CDCl$_3$, 400 MHz) δ 7.27–7.02 (m, 6H), 6.74 (m, 2H), 4.86 (s, br, 1H) 3.72–3.56 (m, 4H), 3.11–3.00 (m, 5H), 2.80 (m, 3H), 2.89 (s, br, 4H), 2.61 (m, 2H), 1.90 (m, 2H); Low resolution MS (ES$^+$) m/e 446.1 (MH$^+$).
Intermediate 21: 4-{2-[(4-fluoro-6-{[3-(4-fluorophenyl)propyl]methylamino}-1,3,5-triazin-2-yl)amino]ethyl}phenol

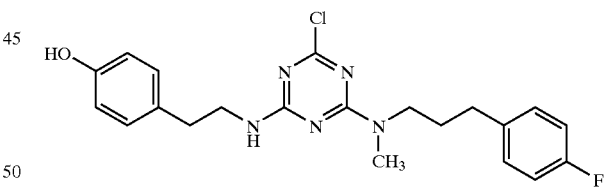

A solution of tyramine (302 mg, 2.3 mmol) and DIEA (299 mg, 2.3 mmol) in DMF (5 mL) was added dropwise to a DMF solution (5 mL) of 2,4-dichloro-6-{[3-(4-fluorophenyl)propyl]methylamino}-1,3,5-triazine (prepared in 92% yield via the procedure outlined for the preparation of Intermediate 13, using N-[3-(4-fluorophenyl)propyl]-N-methylamine, Intermediate 5), (714 mg, 2.3 mmol) in DMF (10 mL). The resulting solution was stirred at RT for 2 h. The solvent was removed under reduced pressure and the resulting residue was diluted with EtOAc (80 mL) and washed with 10% aqueous citric acid (2×40 mL). The organic layer was dried over sodium sulfate and concentrated to give the title compound (950 mg, 100%) as a white solid which was used without further purification: $^1$H NMR (CDCl$_3$, 400 MHz) δ 7.27–6.94 (m, 6H), 6.75 (m, 2H), 5.40–5.32 (d, br, 1H) 3.72–3.56 (m, 4H), 3.11 (m, 3H), 2.78 (m, 2H), 2.62 (m, 2H), 1.92 (m, 2H); Low resolution MS (ES$^+$) m/e 416.4 (MH$^+$).

Intermediate 22: tert-butyl 4-(4-{[3-(4-chlorophenyl)propyl]sulfanyl}-6-{[2-(4-hydroxyphenyl)ethyl]amino}-1,3,5-triazin-2-yl)-1-piperazinecarboxylate

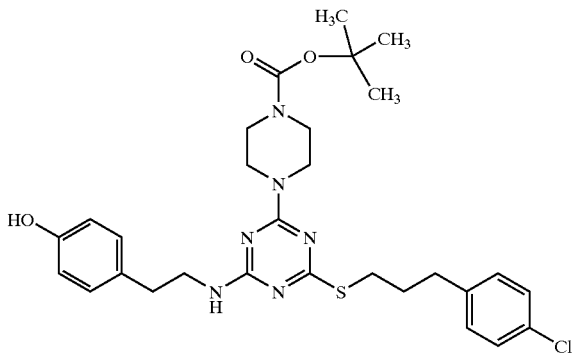

A solution of Intermediate 19 (0.423 g, 0.972 mmol) and BOC-piperazine (0.739 g, 3.968 mmol) in acetonitrile (10 mL) was refluxed for 4 h. The solvent was removed under reduced pressure to give a white residue which was purified by flash chromatography on silica gel (25% EtOAc/hexanes) to give the title compound (0.560 g, 98%) as a white solid. TLC (30% EtOAc/hexanes): $R_f$=0.24; Low resolution MS (ES$^+$) m/e 585 (MH$^+$).

Intermediate 23: 4,6-dichloro-N-[2-(4-methoxyphenyl)ethyl]-1,3,5-triazin-2-amine

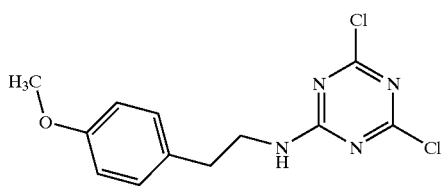

To a cooled (−5° C.) suspension of cyanuric chloride (5.54 g, 30.0 mmol) in CH$_2$Cl$_2$ (150 mL), a mixture of Proton sponge® (6.76 g, 31.5 mmol) and 4-methoxyphenethylamine (4.54 g, 31.5 mmol) was added dropwise over 30 min. After the addition was complete, the resulting mixture was allowed to warm to room temperature and stir for 45 minutes. 10% Aqueous citric acid was added to the reaction mixture and the solution washed with CH$_2$Cl$_2$ (3×100 mL). The combined organic layers were dried over Na$_2$SO$_4$, filtered, and concentrated to a light brown viscous oil which upon standing crystallized to yield an off-white solid (8.97 g, 99%): $^1$H NMR (CDCl$_3$, 400 MHz) δ 7.11 (d, 2H, J=8.5), 6.80 (d, 2H, J=8.6), 5.62 (m, 1H), 3.76 (s, 3H), 3.67–3.59 (m, 2H), 2.80 (t, 2H, J=6.9); TLC (hexanes/EtOAc (9/1)): $R_f$=0.24.

Intermediate 24: 6-chloro-N$^2$-[3-(4-chlorophenyl)propyl]-N$^4$-[2-(4-methoxyphenyl)ethyl]-N$^2$-methyl-1,3,5-triazine-2,4-diamine

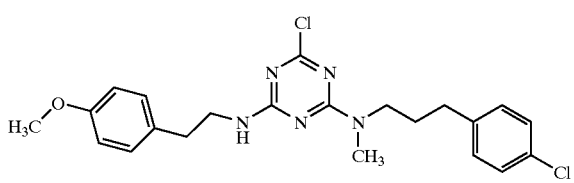

To a cooled (0° C.) solution of Intermediate 23 (7.00 g, 23.4 mmol) in 100 mL of THF a solution of Intermediate 4 (4.54 g, 31.5 mmol) and N,N'-diisopropyl-N-ethylamine (4.07 g, 31.5 mmol) was added dropwise. The reaction mixture was allowed to warm to room temperature and stir for 1 h. Water (100 mL) was added to the reaction mixture and the aqueous layer was extracted with EtOAc (4×100 mL). The combined organic layers were dried over Na$_2$SO$_4$, filtered, and concentrated to a viscous brown oil which crystallized upon standing overnight. The crude material was used without further purification: low resolution MS (ES$^+$) m/e 446 (M$^+$); TLC (hexanes/EtOAc (5/1)): $R_f$=0.35.

Intermediate 25: 4-{2-[(4-chloro-6-{[3-(3,4-difluorophenyl)propyl]methylamino}-1,3,5-triazin-2-yl)amino]ethyl}phenol

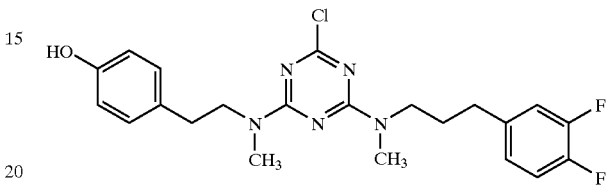

The title compound was prepared as a white solid in 80% yield using tyramine and Intermediate 6 via the procedure outlined for the preparation of Intermediate 21: $^1$H NMR (CDCl$_3$, 400 MHz) δ 7.10–7.00 (m, 5H), 6.75 (m, 2H), 3.76–3.56 (m, 4H), 3.12–3.00 (m, 5.5H), 2.87 (s 0.5H), 2.82 (m, 2H), 2.58 (m, 2H), 1.90 (m, 2H); Low resolution MS (ES$^+$) m/e 448 (MH$^+$).

Intermediate 26: 4-{2-[(4-chloro-6-{[3-(Trifluoromethylphenyl)propyl](methyl)amino]-6-(1-piperazinyl)-1,3,5-triazin-2-yl]methylamino}ethyl)phenol

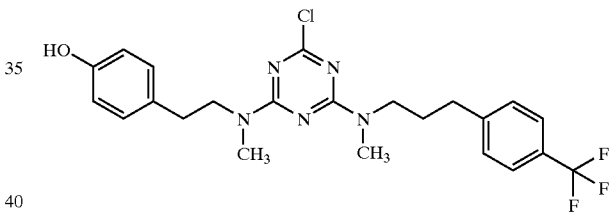

The title compound was prepared as a white solid in 93% yield using tyramine and Intermediate 7 via the procedure outlined for the preparation of Intermediate 21: $^1$H NMR (CDCl$_3$, 400 MHz) δ 7.55 (m, 2H), 7.33–7.23 (m, 2H), 7.09–6.99 (m, 2H), 6.74 (m, 2H), 3.76–3.56 (m, 4H), 3.13–3.00 (m, 6H), 2.79 (m, 2H), 2.68 (m, 2H), 1.94 (m, 2H); Low resolution MS (ES$^+$) m/e 480 (MH$^+$).

Intermediate 27: 4-{2-[(4-chloro-6-{[3-(2,4-dichlorophenyl)propyl]methylamino}-1,3,5-triazin-2-yl)methylamino]ethyl}phenol

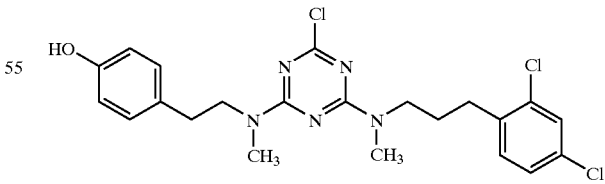

The title compound was prepared as a white solid in 88% yield using tyramine and Intermediate 8 via the procedure outlined for the preparation of Intermediate 21: $^1$H NMR (CDCl$_3$, 400 MHz) δ 7.36–7.01 (m, 5H), 6.75 (m, 2H), 3.74–3.60 (m, 4H), 3.13–3.01 (m, 5H), 2.86–2.76 (m, 3H), 2.70 (m, 2H), 1.90 (m, 2H); Low resolution MS (ES$^+$) m/e 480 (MH$^+$).

EXAMPLE 1

4-(2-{[4-[[3-(4-chlorophenyl)propyl](methyl)amino]-6-(1-piperazinyl)-1,3,5-triazin-2-yl]amino}ethyl)phenol

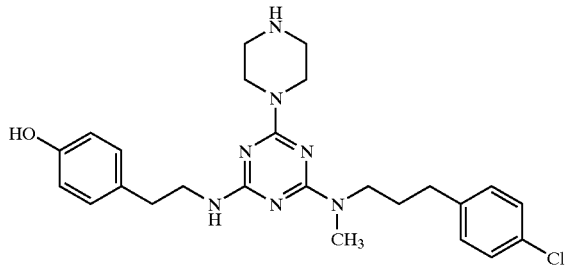

A stirred solution of 1.4 grams (2.4 mmol) of Intermediate 3 in 10 mL of 1,4-dioxane at RT was treated with 25 mL of 4N HCl in 1,4-dioxane. The resulting solution was stirred 18 h at RT then poured into 200 mL of saturated aqueous NaHCO$_3$ and extracted with EtOAc (2×100 mL). The organic layers were combined, dried (MgSO$_4$) and concentrated in vacuo. The residue was purified by silica gel flash column chromatography eluting in gradient fashion first with hexanes/EtOAc 1:1 then chloroform/methanol 9:1 then chloroform/methanol 4:1 to afford a light tan foam. The HCl salt was prepared by dissolution of the free base in EtOAc and addition of 1 M HCl in ether, followed by filtration of the resulting white precipitate and drying at 80° C./20 torr. to afford 925 mgs (80%) of the title compound as a white solid: $^1$H NMR (CD$_3$OD, 400 MHz) δ 7.25 (m, 4H), 7.10 (d, 2H, J=8.0), 6.75 (d, 2H, J=8.4), 4.12 (m, 2H), 3.86 (m, 1H), 3.71 (m, 4H), 3.34 (m, 6H), 3.14 (s, 3H), 2.85 (m, 2H), 2.71 (m, 2H), 2.02 (m, 2H); low-resolution MS (ES$^+$) m/e 483 (MH$^+$), 482 (MH); RP-HPLC (Dynamax C-18 25 cm×4.1 mm; 10–100% CH$_3$CN in H$_2$O with 0.1% TFA buffer; 30 minutes; 1 mL/min) t$_r$=12.68 min, 94% purity.

EXAMPLE 2

4-(2-{[4-methyl{[(1S*,2R*)-2-phenylcyclopropyl]methyl}amino)-6-(1-piperazinyl)-1,3,5-triazin-2-yl]amino}ethyl)phenol.

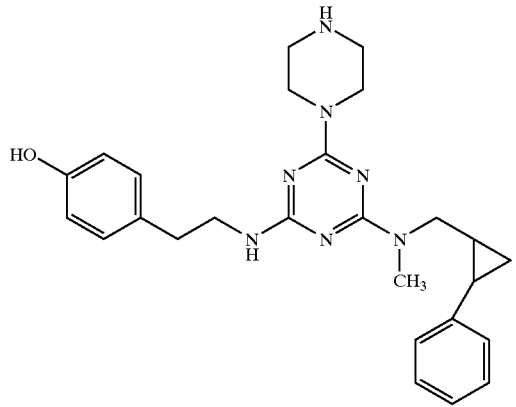

A stirred solution of 100 mg (0.30 mmol) of Intermediate 1 in 4 mL of THF was cooled to 0° C. A solution of 46 mg (0.36 mmol, 1.2 equiv.) of N,N-diisopropylethylamine and 53 mg (0.33 mmol, 1.1 equiv.) of Intermediate 9 in 1 mL of THF was added. The resulting mixture was allowed to warm to RT and 3 h. An excess of polyamine resin HL (200–400 mesh) was added and the reaction was stirred an additional 2 h at RT then heated to 40° C. for 1 h. The resin was filtered off, rinsing with THF and the reaction mixture concentrated in vacuo. The residue was dissolved in 5 mL CH$_3$CN and 100 mg (0.75 mmol, 2.5 equiv.) of tyramine was added as a solid. The reaction mixture was heated to reflux for 16 h, then cooled to RT and concentrated in vacuo. The residue was purified by silica gel flash column chromatography, eluting with hexanes/EtOAc 2:1 to give 65 mg of a white foam. This material was dissolved in 1 mL of THF, cooled to 0° C. and 2 mL of 4 N HCl in 1,4-dioxane was added. The reaction was allowed to warm to RT and stirred 20 h. The crude reaction mixture was then placed directly on a silica gel column and chromatographed eluting in gradient fashion first with chloroform/MeOH 7:1, then chloroform/MeOH 3:1, and finally chloroform/MeOH 2:1 to afford a yellow oil. The HCl salt was generated by dissolving the oil in chloroform, addition of 1 N HCl in ether, filtration of the resulting yellow precipitate, and drying at 50° C. and 20 torr to afford 29 mg (21%) of the title compound as a yellow solid: $^1$H NMR (DMSO-d$_6$, 400 MHz) δ 9.12 (s, br, 1H), 7.25 (m, 5H), 7.03 (d, 2H, J=8.4), 6.68 (d, 2H, J=8.4), 3.87 (m, 4H), 3.64 (m, 4H), 3.14 (m, 2H), 2.92, (m, 2H), 2.85 (s, br, 1H), 2.70 (m, 2H), 2.50 (s, 3H), 2.26 (m, 1H), 1.52 (m, 1H), 1.23 (m, 2H); low-resolution MS (ES$^+$) m/e 461 (MH$^+$), 460 (MH);

EXAMPLE 3

4-[2-({4-[[3-(4-chlorophenyl)propyl](methyl)amino]-6-[4-(3-methoxybenzoyl)-1-piperazinyl]-1,3,5-triazin-2-yl}amino)ethyl]phenol

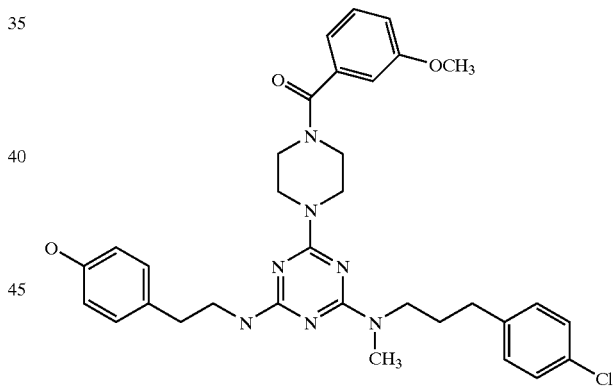

To a solution of 210 mg (0.44 mmol) of 4-(2-{[4-[[3-(4-chlorophenyl) propyl](methyl)amino]-6-(1-piperazinyl)-1,3,5-triazin-2-yl]amino}ethyl)phenol (Example 1) and N,N-diisopropyl-N-ethylamine (0.190 mL, 1.09 mmol) in 5 mL of CH$_2$Cl$_2$ was added 3-methoxybenzoyl chloride (0.064 mL, 0.46 mmol) in 1 mL of CH$_2$Cl$_2$ at 0° C. After 20 min, 10 mL of CH$_2$Cl$_2$ was added and the solution washed with 10 mL each of H$_2$O and brine then dried over Na$_2$SO$_4$. The solvents were removed under reduced pressure and the residue chromatographed on silica gel with hexane/EtOAc 1:2 as eluent to afford 68 mg (26%) of a white glass: $^1$H NMR (CDCl$_3$, 300 MHz) δ 7.34 (t, 1H, J=7.2), 7.25–7.18 (m, 2H), 7.15–7.05 (m, 2H), 7.06–6.96 (m, 5H), 6.68 (d, 2H, J=7.8), 5.10–4.95 (m, 1H), 3.85–3.40 (m, 15H), 3.07 (s, 3H), 2.77 (t, 2H, J=6.3), 2.65–2.50 (m, 2H), 1.95–1.81 (m, 2H); low resolution MS (ES$^+$) m/e 617 (MH$^+$); TLC (hexane/EtOAc (1:2)): R$_f$=0.59.

EXAMPLE 4

4-[2-({4-[[3-(4-chlorophenyl)propyl](methyl)amino]-6-[4-(2-pyridinylcarbonyl)-1-piperazinyl]-1,3,5-triazin-2-yl}amino)ethyl]phenol

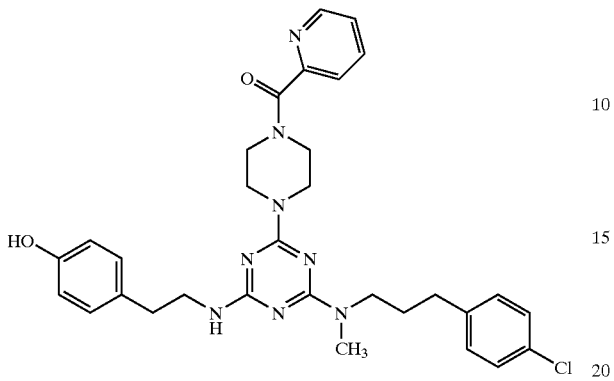

The title compound was prepared in 46% yield via the procedure outlined for Example 3 using 4-(2-{[4-[[3-(4-chlorophenyl)propyl](methyl)amino]-6-(1-piperazinyl)-1,3,5-triazin-2-yl]amino}ethyl)phenol and picolinoyl chloride hydrochloride to give a white glass: $^1$H NMR (CDCl$_3$, 300 MHz) δ 8.65 (bs, 1H), 7.83 (t, 1H, J=7.5), 7.72 (d, 1H, J=7.5), 7.40 (t, 1H, J=5.7), 7.24–7.21 (m, 2H), 7.12–7.04 (m, 4H), 6.73 (d, 2H, J=8.1), 3.96–3.78 (m, 4H), 3.75–3.55 (m, 6H), 3.10 (s, 3H), 2.80 (t, 2H, J=6.6), 2.65–2.60 (m, 2H), 1.95–1.89 (m, 2H); low resolution MS (ES$^+$) m/e 588 (MH$^+$); TLC (CH$_2$Cl$_2$/EtOAc/MeOH (5:5:1)): R$_f$=0.62.

EXAMPLE 5

4-[2-({4-[[3-(4-chlorophenyl)propyl](methyl)amino]-6-[4-(2-pyridinylmethyl)-1-piperazinyl]-1,3,5-triazin-2-yl}amino)ethyl]phenol

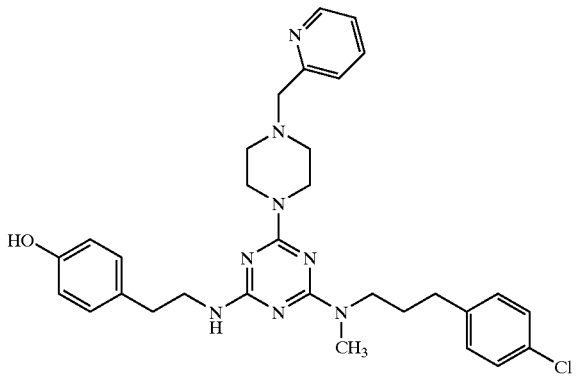

To a solution of 169 mg (0.35 mmol) of 4-(2-{[4-[[3-(4-chlorophenyl) propyl](methyl)amino]-6-(1-piperazinyl)-1,3,5-triazin-2-yl]amino}ethyl)phenol (Example 1) and N,N-diisopropyl-N-ethylamine (0.30 mL, 1.75 mmol) in 5 mL of CH$_2$Cl$_2$ was added 2-chloromethylpyridine hydrochloride (58 mg, 0.35 mmol) and the solution was stirred at room temperature. After 1 hr. 5 mL of CH$_3$CN was added and the solution heated to 80° C. for 5 hr. The reaction was cooled and 15 mL of EtOAc added. The solution was washed with 15 mL each of H$_2$O and brine then dried over Na$_2$SO$_4$. The solvents were removed under reduced pressure and the residue chromatographed on silica gel with CH$_2$Cl$_2$/EtOAc/MeOH 5:5:1 as eluent to afford 91 mg (45%) of a white glass: $^1$H NMR (CDCl$_3$, 400 MHz) δ 8.57 (s, 1H), 7.69–7.60 (m, 1H), 7.43 (d, 2H, J=6.4), 7.24–7.18 (m, 3H), 7.55 (d, 2H, J=7.6), 6.97 (d, 2H, J=8.0), 6.65 (d, 2H, J=8.0), 3.92–2.60 (m, 6H), 3.60–3.45 (m, 4H), 3.03 (s, 3H), 2.73 (t, 2H, J=6.4), 2.56 (m, 2H), 2.44 (m, 4H), 1.84 (m, 2H); low resolution MS (ES$^+$) m/e 574 (MH$^+$); TLC (CH$_2$Cl$_2$/EtOAc/MeOH (5:5:1)): R$_f$=0.52; Anal. calcd. for C$_{31}$H$_{37}$N$_8$OCl: C, 64.40; H, 6.65; N, 19.22. Found: C, 64.46; H, 6.54; N, 19.40.

EXAMPLE 6

4-[2-({4-[[3-(4-chlorophenyl)propyl](methyl)amino]-6-[4-(3-pyridinylmethyl)-1-piperazinyl]-1,3,5-triazin-2-yl}amino)ethyl]phenol

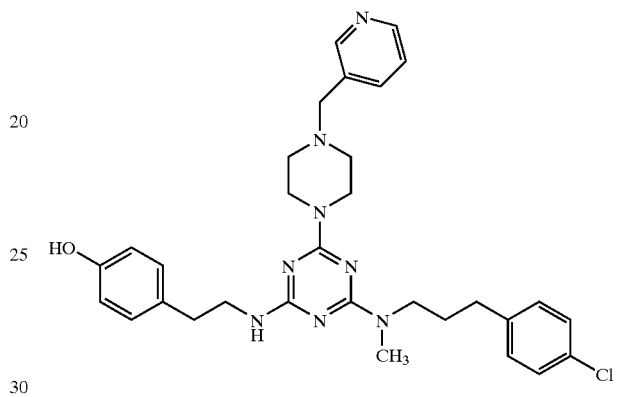

The title compound was prepared in 48% yield via the procedure outlined for Example 5 using 4-(2-{[4-[[3-(4-chlorophenyl)propyl](methyl)amino]-6-(1-piperazinyl)-1,3,5-triazin-2-yl]amino}ethyl)phenol and 3-chloromethyl pyridine hydrochloride to give an off-white glass: $^1$H NMR (CDCl$_3$, 400 MHz) δ 8.49–8.44 (m, 2H), 7.63 (d, 1H, J=7.6), 7.22 (t, 1H, J=4.8), 7.19–7.13 (m, 2H), 7.12–7.01 (m, 2H), 6.94 (d, 2H, J=8.0), 6.63 (d, 2H, J=8.0), 3.85–3.60 (m, 4H), 3.60–3.45 (m, 6H), 2.98 (s, 3H), 2.70 (t, 2H, J=6.4), 0.51 (m, 2H), 2.35 (m, 4H), 1.79(m, 2H); low resolution MS (ES$^+$) m/e 574 (MH$^+$); TLC (CH$_2$Cl$_2$/EtOAc/MeOH (5:5:1): R$_f$=0.43; Anal. calcd. for C$_{31}$H$_{37}$N$_8$OCl: C, 64.96; H, 6.51; N, 19.55. Found: C, 64.72; H, 6.58; N, 19.46.

EXAMPLE 7

4-{2-[(4-[[3-(4-chlorophenyl)propyl](methyl)amino]-6-{4-[(2-methyl-1,3-thiazol-4-yl)methyl]-1-piperazinyl}-1,3,5-triazin-2-yl)amino]ethyl}phenol

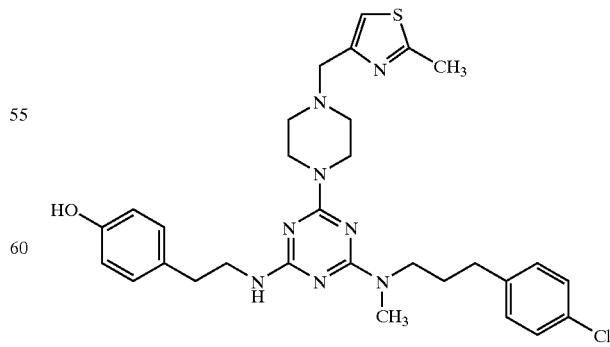

The title compound was prepared in 50% yield via the procedure outlined for example 5 using 4-(2-{[4-[[3-(4- chlorophenyl)propyl](methyl)amino]-6-(1-piperazinyl)-1,3,5-triazin-2-yl]amino}ethyl)phenol and 4-chloromethyl-2-methylthiazole hydrochloride to give an off-white glass: $^1$H NMR (CDCl$_3$, 400 MHz) δ 7.18 (d, 2H, J=8.0), 7.10–7.02 (m, 2H), 6.98–6.95 (m, 3H), 6.64 (d, 2H, J=8.0), 3.85–3.45 (m, 10H), 3.02 (s, 3H), 2.78–2.68 (m, 5H), 2.55–2.50 (m, 2H), 2.50–2.46 (m, 4H), 1.92–1.80 (m, 2H); low resolution MS (ES$^+$) m/e 594 (MH$^+$); TLC (CH$_2$Cl$_2$/EtOAc/MeOH (5:5:1)): R$_f$=0.50; Anal. calcd. for C$_{30}$H$_{37}$N$_8$OSCl: C, 60.74; H, 6.29; N, 18.89. Found: C, 60.64; H, 6.26; N, 18.81.

EXAMPLE 8

(2E)-3-[4-(4-[[3-(4-chlorophenyl)propyl](methyl)amino]-6-{[2-(4-hydroxyphenyl)ethyl]amino}-1,3,5-triazin-2-yl]-1-piperazinyl]-4,4,4-trifluoro-1-phenyl-2-buten-1-one

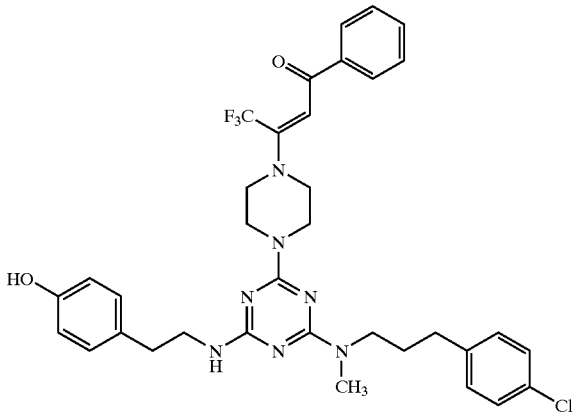

Bromine (1.49 mL, 28.9 mmol) was added dropwise to triphenylphosphine (7.58 g, 28.9 mmol) in 60 mL of CH$_2$Cl$_2$ at 0° C. then stirred for 5 min. The solution was then warmed to room temperature and 4,4,4-trifluoro-1-phenyl-1,3-butanedione (5.0 g, 23.1 mmol) in 25 mL CH$_2$Cl$_2$ was added followed by triethylamine (6.45 mL, 46.3 mmol). The mixture was stirred at room temperature for 2 hr then was washed with 50 mL each of 1 M HCl, H$_2$O, and brine then dried over Na$_2$SO$_4$. The solvent was removed under reduced pressure and the residue chromatographed using hexane/EtOAc 20:1 as eluent to afford 980 mg of a yellowish oil: TLC (hexane/EtOAc (3:1)): R$_f$=0.81. A solution of this material (57 mg, 0.29 mmol) in 1 mL of CH$_2$Cl$_2$ was added to 4-(2-{[4-[[3-(4-chlorophenyl) propyl](methyl)amino]-6-(1-piperazinyl)-1,3,5-triazin-2-yl]amino}ethyl)phenol (Example 1) (127 mg, 0.26 mmol) and N,N-diisopropyl-N-ethylamine (0.23 mL, 1.32 mmol) in 1.5 mL CH$_2$Cl$_2$ and stirred for 1.5 hr at room temperature. The solvent was removed under reduced pressure and the residue chromatographed on silica gel with hexane/EtOAc/CH$_2$Cl$_2$ 2:1:1 as eluent to afford 72 mg (40%) of a yellow glass: $^1$H NMR (CDCl$_3$, 400 MHz) δ 7.89 (d, 2H, J=7.2), 7.51 (t, 1H, J=7.2), 7.49–7.45 (m, 2H), 7.16 (d, 2H, J=8.0), 7.04 (d, 2H, J=7.2), 6.96 (d, 2H, J=8.0), 6.64 (d, 2H, J=7.2), 6.31 (s, 1H), 4.95–4.75(bs, 1H), 3.88–3.65 (m, 4H), 3.19 (m, 4H), 3.00 (s, 3H), 2.73 (t, 2H, J=6.0), 2.62–2.49 (m, 2H), 1.92–1.78 (m, 2H); low resolution MS (ES$^+$) m/e 681 (MH$^+$); TLC (hexane/EtOAc/CH$_2$Cl$_2$ (1:1:1)): R$_f$=0.80; Anal. calcd. for C$_{35}$H$_{37}$N$_7$O$_2$ClF$_3$: C, 61.81; H, 5.48; N, 14.42. Found: C, 61.60; H, 5.46; N, 14.38.

EXAMPLE 9

3-[4-(4-[[3-(4-chlorophenyl)propyl](methyl)amino]-6-{[2-(4-hydroxyphenyl)ethyl]amino}-1,3,5-triazin-2-yl)-1-piperazinyl]-N,N-dimethylpropanamide

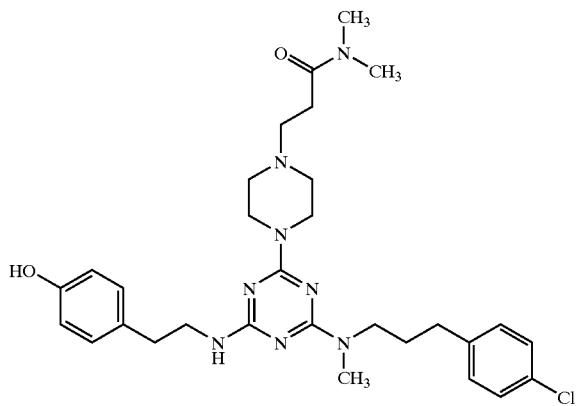

N,N-dimethyl-2-propenamide (0.034 mL, 0.32 mmol) was added to 4-(2-{[4-[[3-(4-chlorophenyl)propyl](methyl)amino]-6-(1-piperazinyl)-1,3,5-triazin-2-yl]amino}ethyl)phenol (Example 1) (156 mg, 0.32 mmol) and N,N-diisopropyl-N-ethylamine (0.28 mL, 1.59 mmol) in 1.5 mL of CH$_2$Cl$_2$ and stirred at room temperature overnight The solvent was removed under reduced pressure and the residue chromatographed on silica gel using EtOAc/CH$_2$Cl$_2$/MeOH 10:10:1 as eluent to afford 132 mg (70%) of an off-white glass: $^1$H NMR (CDCl$_3$, 400 MHz) δ 7.19 (d, 2H, A 7.6), 7.06 (d, 2H, J=6.4), 6.98 (d, 2H, J=7.6), 6.68 (d, 2H, J=6.4), 3.85–3.48 (m, 9H), 3.08–2.92 (m, 7H), 2.88 (s, 3H), 2.82–2.69 (m, 4H), 2.65–2.42 (m, 8H); low resolution MS (ES$^+$) m/e 582 (MH$^+$); TLC (CH$_2$Cl$_2$/EtOAc/MeOH (3:3:1)): R$_f$=0.40; Anal. calcd. for C$_{30}$H$_{41}$N$_8$O$_2$Cl: C, 61.06; H, 7.17; N, 18.99. Found: C, 61.04; H, 7.06; N, 18.95.

EXAMPLE 10

6-({4-(4-methyl-1-piperazinyl)-6-[(3-phenylpropyl)sulfanyl]-1,3,5-triazin-2-yl}amino)-5,6,7,8-tetrahydro-2-naphthalenol

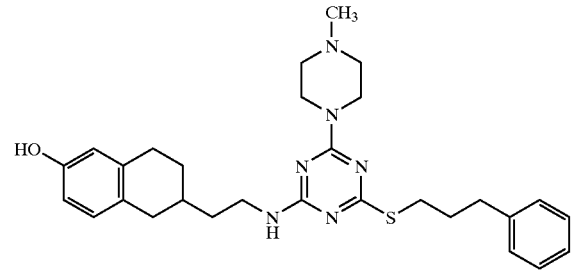

A solution of Intermediate 14 (0.095 g, 0.390 mmol) and DIEA (0.14 mL, 0.780 mmol) in DMF (0.5 mL) was added dropwise to a solution of Intermediate 12 (0.117 g, 0.390 mmol) in acetonitrile (1.5 mL). It was stirred at rt for 8 h. The solvent was removed under reduced pressure and the resulting residue was diluted with EtOAc (10 mL) and washed with 10% aqueous citric acid (3×20 mL). The organic layer was dried over magnesium sulfate, filtered, and concentrated to give an oily residue which was purified by flash chromatography on silica gel (10% EtOAc/hexanes to 20% EtOAc/hexanes gradient solution) to give 0.127 g (76%) as a light yellow solid. (TLC (40% EtOAc/hexanes): $R_f$=0.46). The solid was dissolved in acetonitrile (5 mL) and methylpiperazine (0.16 mL, 1.44 mmol) was added. The resulting solution was then refluxed for 4 h. The solvent was removed under reduced pressure to give an oily residue which was purified by flash chromatography on silica gel (50% EtOAc/hexanes to 100% EtOAc gradient solution) to give the title compound (0.116 g, 82%) as a white solid. TLC (100% EtOAc): $R_f$=0.17. Low resolution MS (ES$^+$) m/e 491 (MH$^+$). RP-HPLC (Dynamax C-18 25 cm×4.1 mm; 10–100% CH$_3$CN in H$_2$O with 0.1% TFA buffer; 30 minutes; 1 mL/min) $t_r$=13.69 min, 97.5% purity.

EXAMPLE 11

4-(2-{[4-{[3-(4-chlorophenyl)propyl]sulfanyl}-6-(1-piperazinyl)-1,3,5-triazin-2-yl]amino}ethyl)phenol

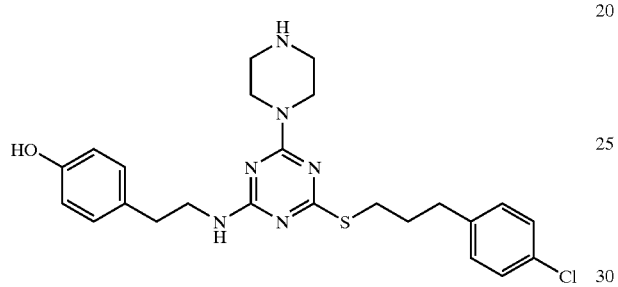

A solution of 4M HCl/dioxane (5 mL) was added to a solution of Intermediate 22 (0.560 g, 0.957 mmol) in dioxane (10 mL). The reaction was stirred for 4 h at RT. The solvents were removed under reduced pressure and the resulting oily residue was triturated (ether) to afford the title compound as a white solid (0.473 g, 93%): Low resolution MS (ES$^+$) m/e 485 (MH$^+$); RP-HPLC (Dynamax C-18 25 cm×4.1 mm; 5–50% CH$_3$CN in H$_2$O with 0.1% TFA buffer; 30 minutes; 1 mL/min) $t_r$=23.57 min, 97.5% purity.

EXAMPLE 12

4-[2-({4-(4-ally-1-piperazinyl)-6-[[3-(4-chlorophenyl)propy](methyl)amino]-1,3,5-triazin-2-yl}amino)ethyl]phenol

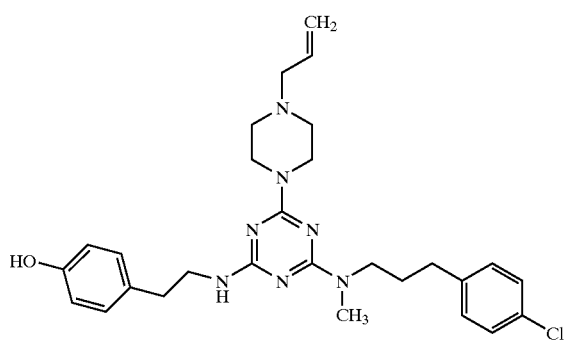

To a solution of Intermediate 24 (0.05 g, 0.112 mmol) in acetonitrile (1 mL), N-allylpiperazine (0.017 g, 0.135 mmol) was added followed by N,N'-diisopropyl-N-ethyl amine (0.025 g, 0.135 mmol). The resulting mixture was stirred overnight at 83° C. The reaction was cooled to RT, then 0.90 mL of a 1 M solution of BBr$_3$ in CH$_2$Cl$_2$ (0.9 mmol) was added and reaction stirred for an additional 3 h. Saturated NaHCO$_3$ (1 mL) and CH$_2$Cl$_2$ (1 mL) was added and the reaction mixture was stirred for 15 min. The organic layer was removed and the aqueous layer washed with CH$_2$Cl$_2$ (3×10 mL). The combined organic layers were concentrated to a brown oil and purified by radial chromatography using a CH$_2$Cl$_2$/MeOH mixture (9:1) to afford (8 mg, 14%) of the title compound as a yellow oil: $^1$H NMR (CDCl$_3$, 400 MHz) δ 7.26–7.00 (m, 4H), 6.98–6.76 (d, 2H, J=7.8), 6.68–6.44 (d, 2H, J=7.7), 5.78–5.68 (m, 1H), 5.24–4.98 (m, 2H), 3.88–3.30 (m, 9H), 3.50 (bs, 4H), 2.80–2.65 (m, 2H), 2.65–2.20 (m, 6H), 2.06 (s, 1H), 1.85 (bs, 1H); low resolution MS (ES$^+$) m/e 522 (M$^+$); TLC (hexanes/EtOAc (4/1)): $R_f$=0.37.

EXAMPLE 13

4-{2-[(4-[[3-(4-chlorophenyl)propyl](methyl)amino]-6-{4-[(2E)-3-phenyl-2-propenyl]-1-piperazinyl}-1,3,5-triazin-2-yl)amino]ethyl}phenol

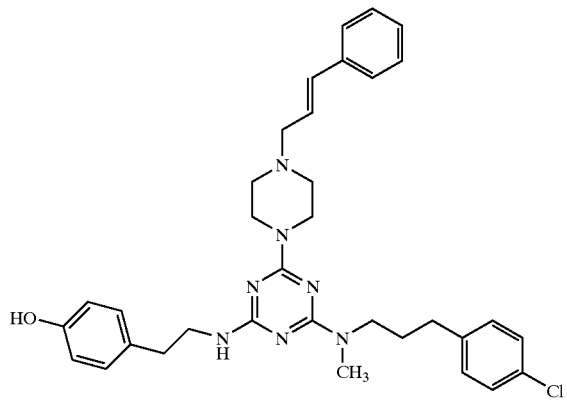

To a solution of Intermediate 24 (0.05 g, 0.112 mmol), N-cinnamylpiperazine (0.027 g, 0.135 mmol) was added followed by N,N'-diisopropyl-N-ethyl amine (0.025 g, 0.135 mmol). The resulting mixture was stirred overnight at 83° C. The reaction was cooled to RT, then 0.90 mL of a 1 M solution of BBr$_3$ in CH$_2$Cl$_2$ (0.9 mmol) was added and reaction stirred for an additional 3 h. Saturated NaHCO$_3$ (1 mL) and CH$_2$Cl$_2$ (1 mL) was added and the reaction mixture was stirred for 15 min. The organic layer was removed and the aqueous layer washed with CH$_2$Cl$_2$(3×10 mL). The combined organic layers were concentrated to a brown oil and purified by radial chromatography using a CH$_2$Cl/MeOH mixture (9:10) to afford the title compound (0.032 g, 48%) as a yellow oil: $^1$H NMR (CDCl$_3$, 400 MHz) δ 7.36 (d, 2H, J=7.5), 7.31 (t, 2H, J=7.4), 7.24 (d, 1H, J=3.5), 7.21 (s, 1H), 7.20 (d, 2H, J=8.2), 7.05 (bs, 2H), 6.94 (d, 2H, J=8.0), 6.62 (d, 2H, J=7.9), 6.52 (d, 1H, J=15.8), 6.34–6.22 (m, 1H), 3.92–3.42 (m, 8H), 3.18 (bs, 2H), 3.02 (bs, 2H), 2.75 (dd, 1H, J=6.5), 2.64–2.38 (m, 6H), 1.57 (bs, 1H); TLC (hexanes/EtOAc (1/1)): $R_f$=0.44.

EXAMPLE 14

4-{2-[[4-[[3-(4-chlorophenyl)propyl](methyl)amino]-6-(1-piperazinyl)-1,3,5-triazin-2-yl](methyl)amino]ethy}phenol

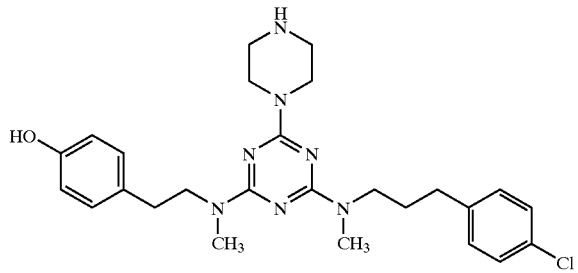

A stirred solution of piperazine (1.29 g, 15 mmol) in isopropanol (11 mL) was treated dropwise with Intermediate 20 (0.223 g, 0.5 mmol) in ethyl acetate (3 mL) at RT. After the addition was complete, the solution was refluxed for 30 min. The solvent was removed under reduced pressure to give a white residue which was triturated with water and extracted with EtOAc (2×30 mL). The organic layers were washed with brine (3×50 mL), dried (MgSO$_4$), and concentrated in vacuo to give the title compound (0.2488 g, 100%) as a white solid: $^1$H NMR (CDCl$_3$, 400 MHz) δ 7.22 (d, 2H, J=8.0), 7.09 (d, 2H, J=8.0), 7.05 (d, 2H, J=8.2), 6.72 (d, 2H, J=8.2), 3.80–3.58 (m, 9H), 3.07 (s, 4H), 3.01 (s, br, 2H), 2.89 (s, br, 4H), 2.78 (m, 2H), 2.59 (m, 2H), 1.88 (m, 2H); low-resolution MS (ES$^+$) m/e 496 (MH$^+$); RP-HPLC (Capeell Pak C-18, 15 cm×4.6 mm; 0–95% CH$_3$CN in H$_2$O with 0.1% TFA buffer; 15 minutes; 1 mL/min) t$_r$=11.92 min, 99% purity.

EXAMPLE 15

4-(2-{[4-[[3-(4-chlorophenyl)propyl](methyl)amino]-6-(4-methyl-1-piperazinyl)-1,3,5-triazin-2-yl](methyl)amino}ethyl)phenol

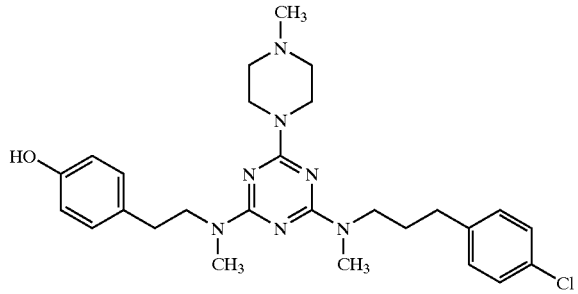

The title compound was prepared in 99% yield via the procedure outlined for Example 14 using N-methylpiperazine to give a white solid: $^1$H NMR (CDCl$_3$, 400 MHz) δ 7.21 (d, 2H, J=7.8), 7.11 (d, 2H, J=7.8), 7.06 (d, 2H, J=8.4), 6.72 (d, 2H, J=8.4), 3.80–3.58 (m, 8H), 3.07 (s, 3H), 3.02 (s, br, 3H), 2.78 (t, 2H, J=7.6), 2.59 (t, 2H, J=7.6), 2.44 (s, br, 4H), 2.33 (s, 3H), 1.88 (m, 2H); low-resolution MS (ES$^+$) m/e 510 (MH$^+$); RP-HPLC (Capeell Pak C-18, 15 cm×4.6 mm; 0–95% CH$_3$CN in H$_2$O with 0.1% TFA buffer; 15 minutes; 1 mL/min) t$_r$=12.17 min. 99% purity.

EXAMPLE 16

4-(2-{[4-[[3-(4-chlorophenyl)propyl](methyl)amino]-6-(3,5-cis-dimethyl-1-piperazinyl)-1,3,5-triazin-2-yl](methyl)amino}ethyl)phenol

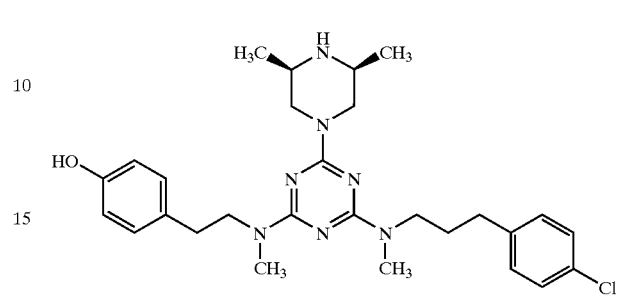

The title compound was prepared in 95% yield via the procedure outlined for Example 14 using cis-2,6-dimethylpiperazine to give a white solid: $^1$H NMR (CDCl$_3$, 400 MHz) δ 7.21 (d, 2H, J=8.0), 7.10 (d, 2H, J=8.0), 7.07 (d, 2H, J=8.4), 6.72 (d, 2H, J=8.4), 4.64 (s, br, 2H)-3.67–3.59 (m, 4H), 3.08 (s, 3H), 3.03 (s, br, 3H), 2.78 (m, 4H), 2.59 (t, 2H, J=8.0), 2.36 (m, 3H), 1.89 (m, 2H), 1.21 (d, 6H, J=6.0); low-resolution MS (ES$^+$) m/e 524 (MH$^+$); RP-HPLC (Capcell Pak C-18, 15 cm×4.6 mm; 0–95% CH$_3$CN in H$_2$O with 0.1% TFA buffer; 15 minutes; 1 mL/min) t$_r$=12.39 min, 99% purity.

EXAMPLE 17

4-{2-[{4-[[3-(4-chlorophenyl)propyl](methyl)amino]-6-[4-(2-hydroxyethyl-1-piperazinyl]-1,3,5-triazin-2-yl}(methyl)amino]ethyl}phenol

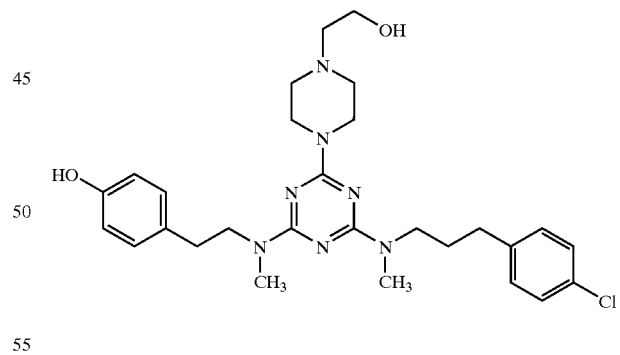

The title compound was prepared in 99% yield via the procedure outlined for Example 14 using 1-(2-hydoxyethyl)piperazine to give a white solid: $^1$H NMR (CDCl$_3$, 400 MHz) δ 7.22 (d, 2H, J=8.0), 7.11 (d, 2H, J=8.0), 7.06 (d, 2H, J=8.4), 6.73 (d, 2H, J=8.4), 3.80–3.58 (m, 10H), 3.08 (s, 3H), 3.02 (s, br, 3H), 2.78 (t, 2H, J=7.6), 2.59 (m, 5H), 2.51 (s, br, 4H), 1.88 (m, 2H); low-resolution MS (ES$^+$) m/e 540 (MH$^+$); RP-HPLC (Capcell Pak C-18 25 cm×4.6 mm; 0–95% CH$_3$CN in H$_2$O with 0.1% TFA buffer; 30 minutes; 1 mL/min) t$_r$=12.08 min, 99% purity.

EXAMPLE 18

4-(2-{[4-[[3-(4-fluorophenyl)propyl](methyl)amino]-6-(1-piperazinyl)-1,3,5-triazin-2-yl]amino}ethyl)phenol

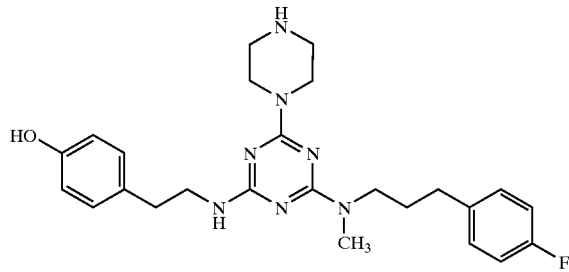

The title compound was prepared in 99% yield from Intermediate 21 via the procedure outlined for Example 14 to give a white solid: $^1$H NMR (CDCl$_3$, 400 MHz) δ 7.11 (s, br, 2H), 7.09 (d, 2H, J=8.4), 6.94 (m, 2H), 6.66 (d, 2H, J=8.4), 4.88 (s, br, 1H) 3.70–3.55 (m, 7H), 3.05 (s, br, 3H), 2.85 (s, br, 5H), 2.76 (m, 2H), 2.58 (m, 2H), 1.86 (m, 2H); low-resolution MS (ES$^+$) m/e 466 (MH$^+$); RP-HPLC (Capcell Pak C-18 25 cm×4.6 mm; 0–95% CH$_3$CN in H$_2$O with 0.1% TFA buffer; 30 minutes; 1 mL/min) t$_r$=10.94 min, 98% purity.

EXAMPLE 19

4-(2-{[4-[[3-(4-fluorophenyl)propyl](methyl)amino]-6-(1-piperazinyl)-1,3,5-triazin-2-yl]methylamino}ethyl)phenol

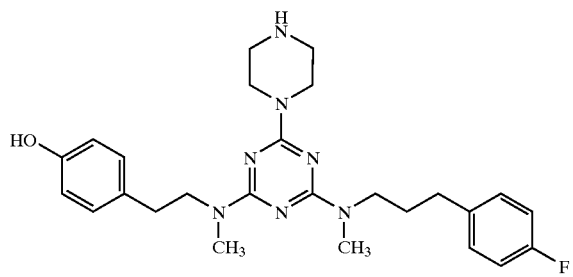

The title compound was prepared in 94% yield via the procedure outlined for Example 14 from 4-{2-[(4-chloro-6-{[3-(4-fluorophenyl)propyl]methylamino}-1,3,5-triazin-2-yl)methylamino]ethyl}phenol to give a white solid: $^1$H NMR (CDCl$_3$, 400 MHz) δ 7.12 (s, br, 2H), 7.05 (d, 2H, J=7.2), 6.94 (m, 2H), 6.72 (d, 2H, J=7.2), 4.88 (s, br, 1H) 3.74–3.58 (m, 9H), 3.08 (s, 3H), 3.05 (s, br, 3H), 2.89 (s, br, 4H), 2.78 (m, 2H), 2.60 (m, 2H), 1.88 (m, 2H); low-resolution MS (ES$^+$) m/e 481 (MH$^+$); RP-HPLC (Capcell Pak C-18 25 cm×4.6 mm; 0–95% CH$_3$CN in H$_2$O with 0.1% TFA buffer; 30 minutes; 1 mL/min) t$_r$=11.64 min, 99% purity.

EXAMPLE 20

4-(2-{[4-[[3-(4-fluorophenyl)propyl](methyl)amino]-6-(4-methyl-1-piperazinyl)-1,3,5-triazin-2-yl]methylamino}ethyl)phenol

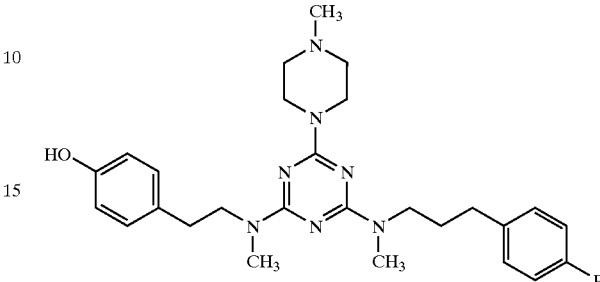

The title compound was prepared in 97% yield via the procedure outlined for Example 14 using 4-{2-[(4-chloro-6-{[3-(4-fluorophenyl)propyl]methylamino}-1,3,5-triazin-2-yl)methylamino]ethyl}phenol and 1-methypiperazine to give a white solid: $^1$H NMR (CDCl$_3$, 400 MHz) δ 7.12 (s, br, 2H), 7.06 (d, 2H, J=8.0), 6.94 (m, 2H); 6.72 (d, 2H, J=8.0), 4.88 (s, br, 1H) 3.79–3.58 (m, 9H), 3.08 (s, 3H), 3.02 (s, br, 3H), 2.78 (m, 2H), 2.60 (t, 2H, J=7.0), 2.45 (s, br, 4H), 2.34 (s, 3H), 1.88 (m, 2H); low-resolution MS (ES$^+$) m/e 495 (MH$^+$); RP-HPLC (Capcell Pak C-18 25 cm×4.6 mm; 0–95% CH$_3$CN in H$_2$O with 0.1% TFA buffer; 30 minutes; 1 mL/min) t$_r$=12.04 min, 99% purity.

EXAMPLE 21

4-(2-{[4-[[3-(3,4-difluorophenyl)propyl](methyl)amino]-6-(1-piperazinyl)-1,3,5-triazin-2-yl]methylamino}ethyl)phenol

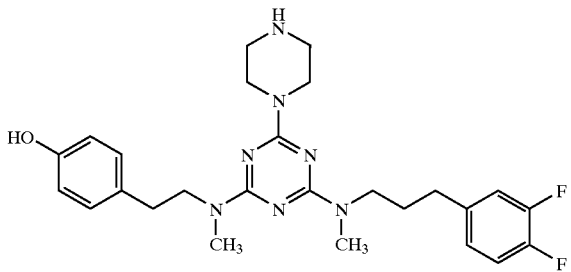

The title compound was prepared in 100% yield from Intermediate 25 via the procedure outlined for Example 14 to give a white solid: $^1$H NMR (CDCl$_3$, 400 MHz) δ 7.05 (d, 2H, J=8.0), 7.01 (m, 2H), 6.87 (m, 1H), 6.72 (d, 2H, J=8.0), 3.74–3.58 (m, 9H), 3.08 (s, 3H), 3.02 (s, br, 3H), 2.90 (s, br, 4H), 2.78 (m, 2H), 2.58 (t, 2H, J=8.0), 1.88 (m, 2H); low-resolution MS (ES$^+$) m/e 498 (MH$^+$); RP-HPLC (Capcell Pak C-18 25 cm×4.6 mm; 0–95% CH$_3$CN in H$_2$O with 0.1% TFA buffer; 30 minutes; 1 mL/min) t$_r$=11.79 min, 99% purity.

EXAMPLE 22

4-(2-{methyl[4-(methyl{3-[4-(trifluoromethyl)phenyl]propyl}amino)-6-(1-piperazinyl)-1,3,5-triazin-2-yl]amino}ethyl)phenol

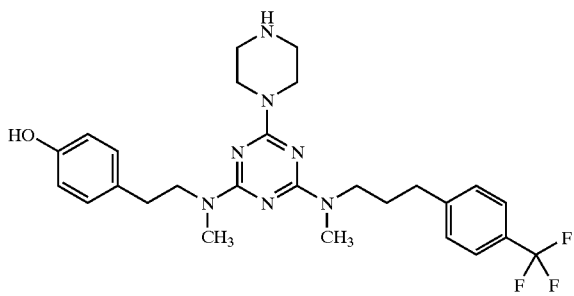

The title compound was prepared in 98% yield from Intermediate 26 via the procedure outlined for Example 14 to give a white solid: $^1$H NMR (CDCl$_3$, 400 MHz) δ 7.55 (d, 2H), 7.32 (d, 2H), 7.05 (d, 2H, J=8.0), 6.75 (d, 2H, J=8.0), 3.79–3.61 (m, 9H), 3.13 (s, 3H), 3.04 (s, br, 3H), 2.93 (s, br, 4H), 2.80 (m, 2H), 2.70 (s, br, 2H), 1.88 (m, 2H); low-resolution MS (ES$^+$) m/e 530 (MH$^+$); RP-HPLC (Capcell Pak C-18 25 cm×4.6 mm; 0–95% CH$_3$CN in H$_2$O with 0.1% TFA buffer; 30 minutes; 1 mL/min) t$_r$=12.40 min, 98% purity.

EXAMPLE 23

4-(2-{[4-[[3-(2,4-dichlorophenyl)propyl](methyl)amino]-6-(1-piperazinyl)-1,3,5-triazin-2-yl]methylamino}ethyl)phenol

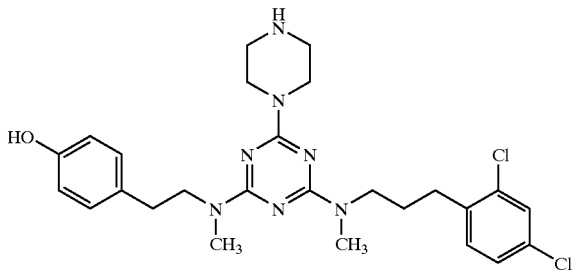

The title compound was prepared in 92% yield from Intermediate 27 via the procedure outlined for Example 14 to give a white solid: $^1$H NMR (CDCl$_3$, 400 MHz) δ 7.34 (s, 1H), 7.13 (s, br, 2H), 7.05 (d, 2H, J=8.0), 6.73 (d, 2H, J=8.0), 3.79–3.61 (m, 9H), 3.09 (s, 3H), 3.02 (s, br, 3H), 2.89 (s, br, 4H), 2.76 (m, 2H), 2.70 (t, 2H, J=8.0), 1.88 (m, 2H); low-resolution MS (ES$^+$) m/e 530 (MH$^+$); RP-HPLC (Capcell Pak C-18, 15 cm×4.6 mm; 0–100% CH$_3$CN in H$_2$O with 0.1% TFA buffer; 15 minutes; 1 mL/min) t$_r$=12.52 min, 99% purity.

EXAMPLE 24

4-[2-({4-[[3-(4-chlorophenyl)propyl](methyl)amino]-6-[4-(2-hydroxyethyl)-1-piperazinyl]-1,3,5-triazin-2-yl}amino)ethyl]phenol

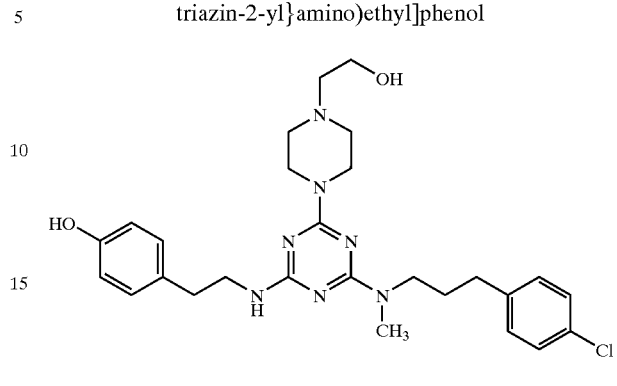

The title compound was prepared in 91% yield via the procedure outlined for Example 14 using 4-[2-({4-chloro-6-[[3-(4-chlorophenyl)propyl](methyl)amino]-1,3,5-triazin-2-yl}amino)ethyl]phenol and 1-(2-hydoxyethyl)piperazine to give a white solid: $^1$H NMR (CDCl$_3$, 400 MHz) δ 7.23 (d, 2H, J=8.0), 7.10 (d, 2H, J=8.0), 7.09 (d, 2H, J=8.0), 6.67 (d, 2H, J=8.0), 4.88(s, br, 1H), 3.80–3.55 (m, 9H), 3.05 (s, br, 3H), 2.77 (t, 2H, J=6.6), 2.57–2.48 (m, 8H), 1.86 (s,br, 2H); low-resolution MS (ES$^+$) m/e 526 (MH$^+$); RP-HPLC (Capcell Pak C-18 25 cm×4.6 mm; 0–95% CH$_3$CN in H$_2$O with 0.1% TFA buffer; 30 minutes; 1 mL/min) t$_r$=11.20 min, 99% purity.

Biological Data

Protein Preparation:

The ligand binding domain of both ERα and ERβ were subcloned into pGEX-2T vector which had been modified to contain KpnI and BamHI restriction sites in the multiple cloning region. GST-hERα and GST-hERβ proteins were made by transforming BL21(DE3)pLYS S competent cells with the appropriate expression plasmid. Liquid cultures containing standard Luria-Bertani (LB) broth with 0.1 mg/ml ampicillin and 0.033 mg/ml chloramphenicol were grown at 37° C. to an OD600 of 0.5–1.0 then induced with IPTG for 2–3 hours. The cells were collected by centrifugation and resuspended in lysis buffer (50 mM Tris pH 7.9; 250 mM KCl; 1% Triton X-100; 10 mM DTT; 1 mM PMSF). The lysate was then placed on dry ice until completely frozen. The frozen lysate was thawed and centrifuged 20 min at 4° C. at 80K rpm in a TLA 100.2 rotor in a Beckman TL-100 ultracentrifuge. The supernatant was retained and glycerol was added to a final concentration of 10%. The protein content of the supernatant was quantitated using the BioRad Protein Assay Reagent The protein was then stored at −80° C. until used in the binding assay.

Competition Binding Assay:

Polylysine coated Yttrium Silicate SPA beads (Amersham #RPNQ 0010) are resuspended in assay buffer [10 mM potassium phosphate buffer pH 7.0 containing 2 mM EDTA, 50 mM NaCl, 1 mM DTT, 2 mM CHAPS, 10% glycerol] to a concentration of 1 g/60 ml. 30 ul (0.5 mg) of the SPA beads are then added to each well of a Packard OptiPlate (Packard 6005190, Packard Instruments, Meriden, Conn.). The ERα or ERβ protein is diluted to the appropriate concentration (empirically determined for each protein prep by generating a protein curve using 0.5 to 10 ug total protein and 1 nM [3H]Estradiol and selecting a protein concentration that does not deplete the radioligand) and added as 30 ul aliquots to each well. [2, 4, 6, 7, 16, 17–3H(N)]-Estradiol is added as a 30 ul aliquot to give a final assay concentration of 1 nM. To give a final volume of 100 ul, either 10 ul of a test compound solution (typically in 10% DMSO as solvent), solvent containing no test compound (to determine total binding, T), or solvent containing 17-b-estradiol at 100 uM (to determine non-specific binding, NS) are finally added to the plate. The plates are shaken vigorously for two hours then counted on a Packard TopCount using the protocol for counting tritium yttrium silicate SPA beads. Data analysis was done by standard methods. % Bound was calculated for each concentration of each test compound using the equation % Bound=100*((Test−NS)/(T−NS)). % Bound was plotted vs concentration and curve fitting was accomplished using non-linear regression.

Saturation Binding Assay:

Saturation binding assays were run similarly to competition assays. Dissociation constants (Kd) were determined by generating twelve-point saturation curves using 10 uM 17-b-estradiol to define nonspecific binding. [2, 4, 6, 7, 16, 17-3H(N)]-Estradiol was added such that the final concentration ranged from 0.1 to 100 nM.

| Example # | Estrogen Receptor Binding[a] | |
|---|---|---|
| | Avg. ER α $pK_i$ (n)[b] | Avg. ER β $pK_i$ (n)[b] |
| 1 | 6.47 (4) | 7.98 (4) |
| 2 | 5.92 (6) | 7.42 (6) |
| 3 | 5.75 (4) | 7.02 (4) |
| 4 | 5.36 (8) | 6.81 (8) |
| 5 | 6.28 (10) | 7.42 (10) |
| 6 | 6.35 (4) | 7.50 (4) |
| 7 | 6.34 (10) | 7.73 (10) |
| 8 | 5.80 (4) | 7.08 (4) |
| 9 | 6.45 (2) | 7.70 (2) |
| 10 | 6.40 (10) | 7.20 (10) |
| 11 | 6.97 (10) | 7.81 (10) |
| 12 | 6.44 (14) | 7.64 (8) |
| 13 | 6.85 (2) | 8.00 (2) |
| 14 | 6.25 (8) | 7.58 (8) |
| 15 | 6.42 (4) | 7.88 (4) |
| 16 | 6.64 (4) | 7.96 (4) |
| 17 | 6.22 (4) | 7.54 (4) |
| 18 | 6.43 (4) | 7.80 (4) |
| 19 | 6.26 (4) | 7.61 (4) |
| 20 | 6.25 (4) | 7.63 (4) |
| 21 | 6.67 (2) | 7.63 (2) |
| 22 | 6.26 (2) | 7.07 (2) |
| 23 | 6.30 (4) | 7.48 (4) |
| 24 | 6.47 (8) | 7.83 (8) |

[a]Values derived from competition binding assay;
[b]$pK_1$ = −log of the concentration of test compound required to achieve an apparent $K_1$ value
n = number of determinations

We claim:

1. A compound selected from the group:
   4-(2-{[4-[[3-(4-chlorophenyl)propyl](methyl)amino]-6-(1-piperazinyl)-1,3,5-triazin-2-yl]amino}ethyl)phenol;
   4-(2-{[4-(methyl{[(1S*,2R*)-2-phenyleyclopropyl]methyl}amino)-6-(1-piperazinyl)-1,3,5-triazin-2-yl]amino}ethyl)phenol;
   4-[2-({4-[[3-(4-chlorophenyl)propyl](methyl)amino]-6-[4-(3-methoxybenzoyl)-1-piperazinyl]-1,3,5-triazin-2-yl}amino)ethyl]phenol;
   4-[2-({4-[[3-(4-chlorophenyl)propyl](methyl)amino]-6-[4-(2-pyridinylcarbonyl)-1-piperazinyl]-1,3,5-triazin-2-yl}amino)ethyl]phenol;
   4-[2-({4-[[3-(4-chlorophenyl)propyl](methyl)amino]-6-[4-(2-pyridinylmethyl)-1-piperazinyl]-1,3,5-triazin-2-yl}amino)ethyl]phenol;
   4-[2-({4-[[3-(4-chlorophenyl)propyl](methyl)amino]-6-[4-(3-pyridinylmethyl)-1-piperazinyl]-1,3,5-triazin-2-yl}amino)ethyl]phenol;
   4-{2-[(4-[[3-(4-chlorophenyl)propyl](methyl)amino]-6-{4-[(2-methyl-1,3-thiazol-4-yl)methyl]-1-piperazinyl}-1,3,5-triazin-2-yl)amino]ethyl}phenol;
   (2E)-3-[4-(4-[[3-(4-chlorophenyl)propyl](methyl)amino]-6-{[2-(4-hydroxyphenyl)ethyl]amino}-1,3,5-triazin-2-yl)-1-piperazinyl]-4,4,4-trifluoro-1-phenyl-2-buten-1-one;
   3-[4-(4-[[3-(4-chlorophenyl)propyl](methyl)amino]-6-{[2-(4-hydroxyphenyl)ethyl]amino}-1,3,5-triazin-2-yl)-1-piperazinyl]-N,N-dimethylpropanamide;
   6-({4-(4-methyl-1-piperazinyl)-6-[(3-phenylpropyl)sulfanyl]-1,3,5-triazin-2-yl}amino)-5,6,7,8-tetrahydro-2-naphthalenol;
   4-(2-{[4-{[3-(4-chlorophenyl)propyl]sulfanyl}-6-(1-piperazinyl)-1,3,5-triazin-2-yl]amino}ethyl)phenol;
   4-[2-({4-(4-allyl-1-piperazinyl)-6-[[3-(4-chlorophenyl)propyl](methyl)amino]-1,3,5-triazin-2-yl}amino)ethyl]phenol;
   4-{2-[(4-[[3-(4-chlorophenyl)propyl](methyl)amino]-6-{4-[(2E)-3-phenyl-2-propenyl]-1-piperazinyl}-1,3,5-triazin-2-yl)amino]ethyl}phenol;
   4-{2-[[4-[[3-(4-chlorophenyl)propyl](methyl)amino]-6-(1-piperazinyl)-1,3,5-triazin-2-yl](methyl)amino]ethyl}phenol;
   4-(2-{[4-[[3-(4-chlorophenyl)propyl](methyl)amino]-6-(4-methyl-1-piperazinyl)-1,3,5-triazin-2-yl](methyl)amino}ethyl)phenol;
   4-(2-{[4-[[3-(4-chlorophenyl)propyl](methyl)amino]-6-(3,5-cis-dimethyl-1-piperazinyl)-1,3,5-triazin-2-yl](methyl)amino}ethyl)phenol;
   4-{2-[{4-[[3-(4-chlorophenyl)propyl](methyl)amino]-6-[4-(2-hydroxyethyl)-1-piperazinyl]-1,3,5-triazin-2-yl}(methyl)amino]ethyl}phenol;
   4-(2-{[4-[[3-(4-fluorophenyl)propyl](methyl)amino]-6-(1-piperazinyl)-1,3,5-triazin-2-yl]amino}ethyl)phenol;
   4-(2-{[4-[[3-(4-fluorophenyl)propyl](methyl)amino]-6-(1-piperazinyl)-1,3,5-triazin-2-yl]methylamino}ethyl)phenol;
   4-(2-{[4-[[3-(4-fluorophenyl)propyl](methyl)amino]-6-(4-methyl-1-piperazinyl)-1,3,5-triazin-2-yl]methylamino}ethyl)phenol;
   4-(2-{[4-[[3-(3,4-difluorophenyl)propyl](methyl)amino]-6-(1-piperazinyl)-1,3,5-triazin-2-yl]methylamino}ethyl)phenol;
   4-(2-{methyl[4-(methyl{3-[4-(trifluoromethyl)phenyl]propyl}amino)-6-(1-piperazinyl)-1,3,5-triazin-2-yl]amino}ethyl)phenol;
   4-(2-{[4-[[3-(2,4-dichlorophenyl)propyl](methyl)amino]-6-(1-piperazinyl)-1,3,5-triazin-2-yl]methylamino}ethyl)phenol; and
   4-[2-({4-[[3-(4-chlorophenyl)propyl](methyl)amino]-6-[4-(2-hydroxyethyl)-1-piperazinyl]-1,3,5-triazin-2-yl}amino)ethyl]phenol;
   or a salt thereof.

2. A pharmaceutical composition, comprising: a therapeutically effective amount of a compound as claimed in claim 1, or a salt, solvate, thereof and one or more of pharmaceutically acceptable carriers, diluems and excipients.

3. A method of treating breast cancer in a mammal, comprising administenng to said mammal a therapeutically effective amount of a compound of claim 1 or a salt thereof.

4. A method of regulating, modulating, or inhibiting estrogen receptors in a mammal, comprising administering to said mammal a therapeutically effective amount of a compound of claim 1 or a salt thereof.

* * * * *

UNITED STATES PATENT AND TRADEMARK OFFICE
CERTIFICATE OF CORRECTION

PATENT NO. : 6,943,162 B2
DATED : September 13, 2005
INVENTOR(S) : Hale et al.

It is certified that error appears in the above-identified patent and that said Letters Patent is hereby corrected as shown below:

Column 41,
Line 53, delete "phenyleyclopropyl" and insert -- phenylcyclopropyl --.

Signed and Sealed this

Twenty-third Day of May, 2006

JON W. DUDAS
*Director of the United States Patent and Trademark Office*